US00RE40387E

(19) United States
(12) Reissued Patent
Bandyopadhyay et al.

(10) Patent Number: US RE40,387 E
(45) Date of Reissued Patent: Jun. 17, 2008

(54) PHARMACEUTICAL COMPOSITIONS, DOSAGE FORMS AND METHODS FOR ORAL ADMINISTRATION OF EPOTHILONES

(75) Inventors: Rebanta Bandyopadhyay, Hyderabad (IN); Timothy M. Malloy, Yardley, PA (US); Andrea Panaggio, West Windsor, NJ (US); Krishnaswamy Srinivas Raghavan, Cranbury, NJ (US); Sailesh Amilal Varia, Princeton Junction, NJ (US); Marvin Barry Cohen, Newtown, PA (US)

(73) Assignee: Bristol-Myers Squibb Company, Princeton, NJ (US)

(21) Appl. No.: 11/149,501

(22) Filed: Jun. 9, 2005

Related U.S. Patent Documents

Reissue of:
(64) Patent No.: 6,576,651
Issued: Jun. 10, 2003
Appl. No.: 10/057,390
Filed: Jan. 25, 2002

U.S. Applications:
( 60) Provisional application No. 60/264,228, filed on Jan. 25, 2001, and provisional application No. 60/290,019, filed on May 11, 2001.

(51) Int. Cl.
*A61K 31/425* (2006.01)
*A61K 31/33* (2006.01)
*A61K 31/497* (2006.01)
*A61K 31/335* (2006.01)

(52) U.S. Cl. ..... 514/365; 514/183; 514/254.07; 514/450

(58) Field of Classification Search ..... None
See application file for complete search history.

(56) References Cited

U.S. PATENT DOCUMENTS

| | | | | |
|---|---|---|---|---|
| 5,977,163 | A | * 11/1999 | Li et al. | 514/449 |
| 6,194,181 | B1 | * 2/2001 | Hofmann et al. | |
| 6,204,388 | B1 | * 3/2001 | Danishefsky et al. | |
| 6,211,412 | B1 | * 4/2001 | Georg et al. | |
| 6,380,395 | B1 | * 4/2002 | Vite et al. | 548/146 |
| 6,441,025 | B2 | * 8/2002 | Li et al. | 514/449 |
| 6,605,599 | B1 | * 8/2003 | Vite et al. | 514/63 |

FOREIGN PATENT DOCUMENTS

| | | |
|---|---|---|
| DE | 4138042.8 | * 5/1993 |
| DE | 19542986.9 | * 5/1997 |
| DE | 19639456.2 | * 5/1997 |
| DE | 19636343.8 | * 3/1998 |
| DE | 19645361.5 | * 4/1998 |
| DE | 19645362.3 | * 4/1998 |
| DE | 19647580.5 | * 5/1998 |
| DE | 19701758 | * 7/1998 |
| DE | 19707505.3 | * 9/1998 |
| DE | 19713970 | * 10/1998 |
| DE | 19720312 | * 11/1998 |
| DE | 19821954 | * 11/1998 |
| DE | 19726627 | * 12/1998 |
| EP | 879 605 | * 11/1998 |
| WO | WO 93/10121 | * 5/1993 |
| WO | WO 97/19086 | * 5/1997 |
| WO | WO 98/08849 | * 3/1998 |
| WO | WO 98/22461 | * 5/1998 |
| WO | WO 98/24427 | * 6/1998 |
| WO | WO 98/25929 | * 6/1998 |
| WO | WO 98/38192 | * 9/1998 |
| WO | WO 98/47891 | * 10/1998 |
| WO | WO 99/01124 | * 1/1999 |
| WO | WO 99/02514 | * 1/1999 |
| WO | WO 99/03848 | * 1/1999 |
| WO | WO 99/07692 | * 2/1999 |
| WO | WO 99/27890 | * 6/1999 |
| WO | WO 99/39694 | * 8/1999 |
| WO | WO 99/42602 | * 8/1999 |
| WO | WO 99/43320 | * 9/1999 |
| WO | WO 99/43653 | * 9/1999 |
| WO | WO 99/54319 | * 10/1999 |
| WO | WO 99/67252 | * 12/1999 |
| WO | WO 00/00485 | * 1/2000 |
| WO | WO 00/31247 | * 6/2000 |
| WO | WO 00/37473 | * 6/2000 |
| WO | WO 00/49021 | * 8/2000 |
| WO | WO 00/66589 | * 11/2000 |
| WO | WO 02/058699 | 8/2002 |
| WO | WO 02/058700 | 8/2002 |
| WO | WO 02/072085 | 9/2002 |

OTHER PUBLICATIONS

Martindale, The Extra Pharmacopoeia, 28$^{th}$ edition, published 1982 by the Pharmaceutical Press, pp. 640–641.*
Medline Abstract No. 97217050, Kumar, Indian Journal of Experimental Biology, (May 1996) 34(5), 391–402.*
Medline Abstract No. 97074593, Smith et al., CA: A Cancer Journal for Clinicians, (Nov.–Dec. 1996), 46(6), 343–63.*
Medline Abstract No. 1998029329, Rickels et al., Journal of Clinical Psychiatry, (1997) 58 Suppl. 11, 4–10.*
Medline Abstract No. 96432582, Oka et al., Japanese Journal of Pharmacology, (Jun. 1996) 71(2), 89–100.*
Cecil Textbook of Medicine, 21$^{st}$ Edition, vol. 1, published 2000 by W. B. Saunders Company, pp. 1060–1074.*
U.S. Appl. No. 08/856,533, Nicolaou et al., filed May 14, 1997.*
U.S. Appl. No. 08/923,869, Nicolaou et al., filed Sep. 4, 1997.*
U.S. Appl. No. 60/032,864, Nicolaou et al., filed Dec. 13, 1996.*

(Continued)

*Primary Examiner*—Raymond J. Henley, III
(74) *Attorney, Agent, or Firm*—Hong Liu; Gary D. Greenblatt; Anastasia P. Winslow

(57) ABSTRACT

The invention relates to methods of increasing the bioavailability of orally administered epothilones. Epothilones administered by the methods of the invention are sufficiently bioavailable to have a pharmacological effect. The invention further relates to pharmaceutical compositions, pharmaceutical dosage forms, and kits for use in the methods of the invention.

54 Claims, 2 Drawing Sheets

OTHER PUBLICATIONS

Balog, A., et al., "Total Synthesis of (−)–Epothilone A", *Angew. Chem. Int. Ed. Engl.,*vol. 35, No. 23/24, 2801–2803 (1996).*

Bertini, F., et al., "Alekens from Epoxides by Reductive Elimination with Magnesium Bromide–Magnesium Amalgam", *Chem. Commun.,* 144 (1970).*

Bollag, D.M., et al., "Epothilones, A New Class of Microtubule–stabilizing Agents with a Taxol–like Mechanism of Action", *Cancer Res.* 55, No. 11, 2325–2333 (1995).*

Fujisawa, T., et al., "Deoxygenation of Epoxides to Olefins with $FeCI_2$—n–BuLi System", *Chem. Lett.,* 883–886 (1974).*

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.,* vol. 43, No. 12, 2477–2479 (1978).*

Gladysz, J. A., et al., "Deoxygenation of Epoxides by Metal Atom Cocondensation", *J. Org. Chem.,* vol. 41, No. 22, 3647–3648 (1976).*

Holfe, G., et al., "Epothilone A and B —Novel 16–Membered Macrolides with Cytotoxic Activity: Isolation, Crystal Structure, and Conformation in Solution", *Angew. Chem. Int. Ed. Engl.,* vol. 35, no. 13/14, 1567–1569 (1996).*

Hofle, G., et al., "N–Oxidation of Epothilone A–C and O–Acyl Rearrangement to C–19 and C–21–Substituted Epothilones", *Angew. Chem. Int. Ed.,* vol. 38, No. 13/14, 1971–1974 (1999).*

Inokuchi, T., et al., "Opening of Epoxides to Olefins or Halohydrins with Vanadium(ii)–Tetrahydrofurofuran or Vanadium(III)–Tetrahydrofuran Complexes", *Synlett,* No. 6, 510–512 (1992).*

Kowalaski. R. J., et al., "Activities of the Microtubule–stabilizing Agents Epothilones A and B with Purified Tubulin and in Cells Resistant to Paclitaxel (Taxol®)" *J. Biol. Chem.,* vol. 272, No. 4, 2534–2541 (1997).*

Kupchan, S. M., et al., "Reductive Elimination of Epoxides to Olefins with Zinc–Copper Couple", *J. Org. Chem.,* vol. 36, No. 9, 1187–1190 (1971).*

Martin, M. G., et al., "Epoxides as Alkene Protecting Goups. A Mild and Efficient Deoxygenation", *Tetrahedron Letters,* vol. 25, No. 3, 251–254 (1984).*

McMurry, J. E., et al., "Reduction of Epoxides to Olefins with Low Valent Titanium", *J. Org. Chem.,* vol. 40, No. 17, 2555–2556 (1975).*

McMurry, J. E., et al., "Some Deoxygenation Reactions with Low–Valent Titanium ($TiCI_3/LiAIH_4$)", *J. Org. Chem.,* vol. 43, No. 17, 3249–3254 (1978).*

Meng, D., et al., "Remote Effects in Macrolide Formation Through Ring–Forming Olefin Methathesis: An Application to the Synthesis of Fully Active Epothilone Congeners", *J. Am. Chem. Soc.,* vol. 119, No. 11, 2733–2734 (1997).*

Nicolaou, K. C., et al., "An Approach to Epothilones Based on Olefin Methathesis",*Angew. Chem. Int. Ed. Engl.,* vol. 35, No. 20, 2399–2401 (1996).*

Nicolaou, K. C., et al., "Total Synthesis of Epothilone A: The Macrolactonization Approach", *Angew. Chem. Int. Ed. Engl.,* vol. 36, No. 5, 525–527 (1997).*

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.,* vol. 36, No. 19, 2097–2103 (1997).*

Nicolaou, K. C., et al., "The Olefin Methathesis Approach to Epothilone A and Its Analogues", *J. Am. Chem. Soc.,* vol. 119, No. 34, 7960–7973 (1997).*

Nicolaou, K. C., et al., "Total Synthesis of Epothilones A and B via a Macrolactonization–Based Strategy", *J. Am. Chem. Soc.,* vol. 119, No. 34, 7974–7991 (1997).*

Nicolaou, K. C., et al., "Synthesis of Epothilones A and B in Solid and Solution Phase", *Nature,* vol. 387, 268–272 (1997).*

Nicolaou, K. C., et al., "Synthesis of Epothilones A and B in Solid and Solution Phase" (Correction to *Nature* 387, 268–272 (1997)), *Nature,* 390, 100 (1997).*

Raucher, S., et al., "Total Synthesis of (+)–Dihydrocostunolide via Tandem Cope–Claisen Rearrangement", *J. Org. Chem.,* vol. 51, No. 26, 5503–5505 (1986).*

Sato, M., et al., "Reduction of Organic Compounds with Low–Valent Niobium ($NbCl_5/NaAlH_4$)" *Chem. Letters,* 157–160 (1982).*

Schnizer, D., et al., "Total Synthesis of (−)–Epothilone A", *Angew Chem. Int. Ed. Engl.,* vol. 36, No. 5, 523–524 (1997).*

Schobert, R., et al., "Reduction and Isomerization of Oxiranes and α–Diazoketones by Various Early Transition Metallocenes", *Synlett,* vol. 8, 465–466 (1990).*

Sharpless, K. B., et al., "Lower Valent Tungsten Halides. A New Class of Reagents for Deoxygenation of Organic Molecules", *J. Amer. Chem. Soc.,* vol. 94, No. 18, 6538–6540 (1972).*

Su, D.–S., et al., "Total Synthesis of (−)–Epothilone B: An Extension of the Suzuki Coupling Method and Insights into Structure–Activity Relationships of the Epothilones", *Angew. Chem. Int. Ed. Engl.,* vol. 36, No. 7, 757–759 (1997).*

Su, D.–S, et al., "Structure–Activity Relationships of the Epothilones and the First In Vivo Comparison with Paclitaxel", *Angew. Chem. Int. Ed. Engl.,* vol. 36, No. 19, 2093–2096 (1997).*

Victory, S. F., et al., "Relative Stereochemistry and Solution Conformation of the Novel Paciltaxel–Like Antimitotic Agent Epothilone A", *Bioorg. Med. Chem. Letts.,* vol. 6, No. 7, 893–898 (1996).*

Winkler, J. D., et al., "A Model For The Taxol (Paclitataxel)/Epothilone Pharmacophore", *Bioorg. Med. Chem. Letts.,* vol. 6, No. 24, 2963–2966 (1996).*

Yang, Z., et al., "Total Synthesis of Epothilone A: The Olefin Metathesis Approach",*Angew. Chem. Int. Ed. Engl.,* vol. 36, No. 1/2, 166–168 (1997).*

Bollag, D., et al., "Epothilone, A New Structural Class of Microtubule Stabilizer", Abstract, *Proc. Am. Assoc. Cancer Res.,* vol. 36, 86 Meet. 454 (1995).*

Bollag, D., "Epothilones: Novel Microtubule–Stabilising Agents", *Expert Opin. Invest. Drugs,* vol. 6, No. 7, 867–873 (1997).*

Bertinato, P., et al., "Studies Toward a Synthesis of Epothilone A: Stereocontrolled Assembly of the Acyl Region and Models for Macrocyclization", *J. Org. Chem.,* vol. 6, No. 23, 8000–8001 (1996).*

*Chemical & Engineering News,* "Epothilone Epiphany: Total Synthesis", vol. 74, No. 52, 24–26 (1996).*

*Chemical & Engineering News,* "First Total Synthesis of Epothilone B", vol. 75, No. 13, 23 (1997).*

*Chemical & Engineering News,* "Solid–Phase Epothilone Synthesis Used to Create Analog Library", vol. 75, No. 20, 33 (1997).*

Claus, E., et al., "Sythesis of the C1–C9 Segment of Epothilons", *Tetrahedron Lett.,* vol. 38, No. 8, 1359–1362 (1997).*

De Brabander, J., et al., "Towards a Synthesis of Epothilone A: Rapid Assembly of the C1–C6 and C7–C12 Fragments", *Synlett,* vol. 7, 824–826 (1997).*

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.,* vol. 38, No. 8, 1363–1366 (1997).*

Gerth, K., et al., "Epothilons A and B: Antifungal and Cytotoxic Compounds from *Sorangiusm cellulosum* (Myxobacterial) Production, Physico–chemical and Biological Properties", *J. Antibiotics,* vol. 49, No. 6, 560–563 (1996).*

Marshall, A., "Total Synthesis of Epothilone", *Nature Biotechnology,* vol. 15, No. 3, 205 (1997).*

Meng, D., et al., "Studies Toward a Synthesis of Epothilone A: Use of Hydropyran Templates for the Management of Acyclic–Stereochemical Relationships", *J. Org. Chem.,* vol. 61, No. 23, 7998–7999 (1996).*

Meng, D., et al., "Total Synthesis of Epothilones A and B", *J. Am. Chem. Soc.,* vol. 119, No. 42, 10073–10092 (1997).*

Mensching, S., and Kalesse, M., "Generation of Thiazoles by Colmn Dehydrogenation of Thiazolidines with $MnO_2$", *J. Parkt. Chem.,* vol. 339, No. 1, 96–97 (1997).*

Mulzer, J. and Mantoulidis, A., "Synthesis of the C(1)–C(9) Segment of the Cytotoxic Macrolides Epothilon A and B", *Tetrahedron Lett.,* vol. 37, No. 51, 9197–9182 (1996).*

Nicolaou, K., et al., "Chemistry, Biology and Medicine of Selected Tubulin Polymerizing Agents", *Pure Appl. Chem.,* vol. 71, No. 6, 989–997 (1999).*

Nicolaou, K., et al., "Total Synthesis of Epothilone E and Related Side–chain Modified Analogues Via a Stille Coupling Based Strategy", *Bioorg. Med. Chem.,* vol. 7, No. 5, 665–697 (1999).*

Schinzer, D., et al., "Studies Towards the Total Synthesis of Epothilones: Asymmetric Synthesis of the Key Fragments", *Chem. Eug. J.,* vol. 2, No. 22, 1477–1482 (1996).*

Taylor, R., and Haley, J., "Towards the Synthesis of Epothilone A: Enantioselective Preperation of the Thiazole Sidechain and Macrocyclic Ring Closure", *Tetrahedron Lett.,* vol. 38, No. 12, 2061–2064 (1997).*

Schinzer, D., et al., "Synthesis of (–)–Epothilone A", *Chem. Eug. J.,* vol. 5, No. 9, 2483–2491 (1999).*

Schinzer, D., et al., "Synthesis of (–)–Epothilone B", *Chem. Eur. J.,* vol. 5, No. 9, 2492–2500 (1999).*

Nicolaou, K. C., et al., "Synthesis and Biological Properties of C12, 13–Cyclopropylepothilone A and Related Epothilones", *Chemistry & Biology,* vol. 5, No. 7, 365–372 (1998).*

Altmann, K.H., et al., "Epothilones and Related Structures—A New Class of Microtubule Inhibitors With Patent In Vivo Antitumor Activity," Biochim. Biophys Acta, 1470 (2000).*

Nicolaou et al., "Total Synthesis of Epothilone E and Analogs with Modified Side Chains Through The Stille Coupling Reaction", Angew. Chem. Int. Ed. 37, 84–87 (1998).*

Nicolaou et al., "Total Synthesis of Oxazole– and Cyclopropane–Containing Epothilone B Analogues by the Macrolactonization Approach", Chemistry, European Journal, vol. 3, No. 12, 1971–1986 (1997).*

Nicolaou et al., "Chemical Biology of Epothilones", Angew. Chem. Int. Ed., 37, 2014–2045 (1988).*

* cited by examiner

PHARMACEUTICAL COMPOSITIONS, DOSAGE FORMS AND METHODS FOR ORAL ADMINISTRATION OF EPOTHILONES

Matter enclosed in heavy brackets [ ] appears in the original patent but forms no part of this reissue specification; matter printed in italics indicates the additions made by reissue.

CROSS-REFERENCE TO RELATED APPLICATIONS

This application *is a reissue application of U.S. Pat. No. 6,576,651 B2, which issued from U.S. application Ser. No. 10/057,390, filed Jan. 25, 2002, which* claims priority from provisional application serial No. 60/264,228, filed Jan. 25, 2001 and No. 60/290,019, filed May 11, 2001, incorporated herein by reference in [its] *their* entirety.

FIELD OF THE INVENTION

The invention relates to methods of orally administering epothilones to a patient in a manner that increases bioavailability. The invention further relates to pharmaceutical compositions, pharmaceutical dosage forms, and kits for use in the methods of the invention. In particular, the invention relates to a solid oral dosage form of an epothilone.

BACKGROUND OF THE INVENTION

Epothilones are 16 member cyclic macrolide molecules which find utility in the pharmaceutical field. For example, Epothilone A and B are naturally occurring compounds that can be isolated from certain microorganisms; there two compounds have the following structures:

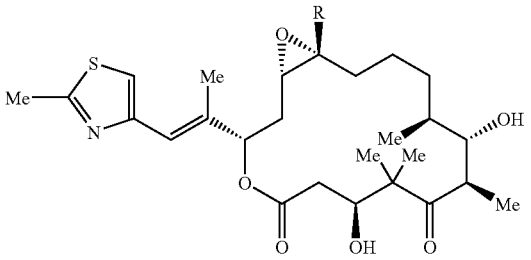

Epothilone A R = H
Epothilone B R = Me

Since the introduction of epothilones into the art, many groups have been designing, synthesizing and testing analogs of the naturally occurring epothilones in an attempt to develop useful pharmaceuticals. (See, e.g., D. Schinzer et al., Angew. Chem. Int. Ed. Engl., 1997, 36, No. 3, 523–524; K. C. Nicolaou, et al., J. Amer. Chem. Soc., 1997, 119, 7974–7991; K. C. Nicaloau et al., Angew. Chem. Int. Ed. Engl., 1996, 35, No. 20, 2399–2401; A. Balog et al., Angew. Chem. Int. Ed. Engl., 1996, 35, No. 23/24, 2801–2803).

Known epothilones exert microtubule-stabilizing effects similar to Taxol® and therefore exhibit cytotoxic activity against rapidly proliferating cells, such as occur in cancer and other hyperproliferative cellular diseases (See Angew. Chem. Int. Ed. Engl., Vol. 35, No. 13/14, 1996 and D. M. Bollag, Exp. Opin. Invest. Drugs, 6(7): 867–873, 1997).

Before epothilones can be used to treat diseases in patients, however, they must be formulated into a pharmaceutical composition that can be administered to the patient; for example, into a dosage form suitable for oral, mucosal (e.g., nasal, sublingual, vaginal, buccal, or rectal), parenteral (e.g., subcutaneous, intravenous, bolus injection, intramuscular, or intraaterial), or transdermal administration. Formulations for oral administration are particularly preferred since they are more convenient and easier to administer than other formulations. Also, the oral route of administration avoids the pain and discomfort of parenteral administration. Accordingly, formulations for oral administration are preferred by patients and result in better patient compliance with dosing schedules.

The usefulness of an oral formulations, however, requires that the active agent be bioavailable. Bioavailability of orally administered drugs is affected by various factors including, for example, drug absorption throughout the gastrointestinal tract, stability of the drug in the gastrointestinal tract, and the first pass effect. Thus, effective oral delivery of an active agent requires that the active agent have sufficient stability in the stomach and intestinal lumen to pass through the intestinal wall. Many drugs, however, tend to degrade quickly in the intestinal tract or have poor absorption in the intestinal tract so that oral administration is not an effective method for administering the drug.

Pharmaceutical compositions intended for oral administration are typically solid dosage forms (e.g., tablets) or liquid preparations (e.g., solutions, suspensions, or elixirs). Solid dosage forms, however, can impose restrictions on the pharmaceutical use of the active agent since some patient populations have difficulty, either physical or psychological, in swallowing solid oral dosage forms. If a liquid dosage form is available, these patients could more easily take the required dose of active ingredient by having it administered in the form of an oral liquid preparation that they can drink or having it administered, for example, by a naso-gastric tube. Thus, liquid oral dosage forms are desirable.

Liquid oral pharmaceutical compositions require a suitable solvent or carrier system to dissolve or disperse the active agent to enable the composition to be administered to a patient The solvent system must be compatible with the active agent and be non-toxic to the patient Commonly, the solvent for liquid oral formulations is a water based solvent.

The formulation of certain epothilones presents difficulties in addition to the normal hurdles, in that certain epothilones are either or both acid labile and/or poorly soluble in aqueous media, which is the media of first choice for oral solutions. The present invention, however, overcomes these difficulties and provides methods and pharmaceutical formulations for the oral administration of epothilones wherein the epothilones are sufficiently bioavailable to have a pharmacological effect.

SUMMARY OF THE INVENTION

The present invention encompasses a method of orally delivering epothilones to a mammal while reducing or avoiding the degradation, decomposition, or deactivation of the epothilone by the gastrointestinal system, particularly by gastric fluid in the stomach. In one embodiment, the method encompasses administering the epothilone in, or with, a pharmaceutically acceptable acid neutralizing buffer. In a preferred embodiment, the administration comprises the use of two solutions, one comprising the active epothilone alone, or in a pharmaceutically acceptable carrier, and the other comprising the pharmaceutically acceptable neutralizing buffer.

The invention therefore includes pharmaceutical compositions comprising an epothilone either in a solid form which is suitable for constitution, or reconstitution if lyophilized, into a pharmaceutically acceptable solution or as a pre-made solution. The invention also encompasses pharmaceutical compositions comprising a pharmaceutically acceptable neutralizing buffer either in solid form suitable for constitution, or reconstitution if lyophilized, into a pharmaceutically acceptable solution or as a pre-made solution.

In a more specific embodiment, the present invention is directed to methods of increasing the bioavailability of an orally administered epothilone. The methods involve orally administering one or more epothilones of Formula:

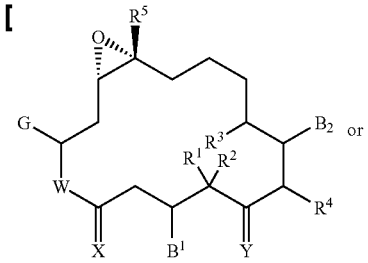

or

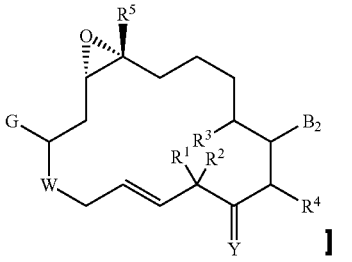

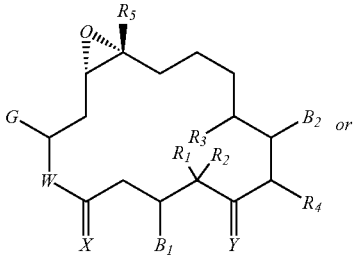

or

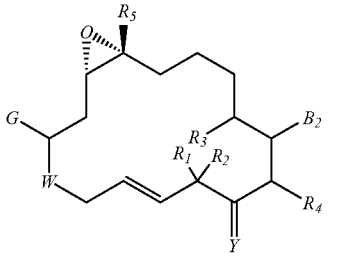

wherein:

G is [selected from the group consisting of] alkyl, substituted alkyl, aryl, substituted aryl, heterocyclo,

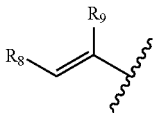

,

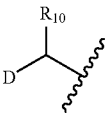

or

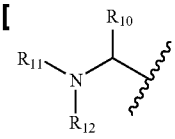

-continued

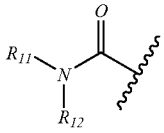

;

W is O or $NR^{16}$;

X is O; S; $CHR_{17}$; or H, $R_{18}$;

Y is [selected from the group consisting of] O; H, H; H, $OR_{22}$; $OR_{23}$, $OR_{23}$; $NOR_{24}$; H, [$NOR_{25}$] $NHOR_{25}$; H, [$HNR_{26}R_{27}$] $NR_{26}R_{27}$; [$NHNR_{28}R_{29}$;] H, $NHNR_{30}R_{31}$ or $CHR_{32}$, where $OR_{23}$, $OR_{23}$ can be a cyclic ketal;

$B_1$ and $B_2$ are [selected from the group consisting of] *independently* H, $OR_{33}$, $OCOR_{34}$, $OCONR_{35}R_{36}$, $NR_{37}R_{38}$, or $NR_{39}CONR_{40}R_{41}$;

D is [selected from the group consisting of] $NR_{42}R_{43}$ or heterocyclo;

$R_1$, $R_2$, $R_3$, $R_4$, and $R_5$ are [selected from] *independently* H[,] *or* lower alkyl;

$R_8$, $R_9$, $R_{10}$ and $R_{11}$ are [selected from the group consisting of] *independently* H, alkyl, substituted alkyl, aryl, substituted aryl, cycloalkyl, heterocyclo or substituted heterocyclo;

$R_{17}$, $R_{18}$, $R_{22}$, and $R_{23}$ are [selected from the group consisting of] *independently* H, alkyl, [and] *or* substituted alkyl;

$R_{24}$, $R_{25}$, $R_{26}$, [$R_{28}$,] $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{51}$, $R_{52}$, *and* $R_{53}$[, and $R_{61}$] are [selected from the group of] *independently* H, alkyl, substituted alkyl, aryl or substituted aryl;

$R_{12}$, $R_{16}$, $R_{27}$, [$R_{29}$,] $R_{31}$, $R_{38}$, and $R_{43}$[,] are [selected from the group consisting of] *independently* H, alkyl, substituted alkyl, substituted aryl, cycloalkyl, heterocyclo, $R_{51}C{=}O$, $R_{52}OC{=}O$, $R_{53}SO_2$, hydroxy, and O-alkyl or O-substituted alkyl[,]*;* or a pharmaceutically acceptable salt, solvate, hydrate, clathrate or prodrug thereof; and orally administering one or more pharmaceutically acceptable acid neutralizing buffers.

The pharmaceutically acceptable acid neutralizing buffer may be administered concurrently with, before, after, or both before and after administration of the one or more epothilones of interest. When administered before the active epothilone, the pharmaceutically acceptable acid neutralizing buffer is administered not more than about 1 hour before the epothilone is administered. When administered after, the pharmaceutically acceptable acid neutralizing buffer is administered not more than about 1 hour after the epothilone is administered.

The pharmaceutically acceptable acid neutralizing buffer solution, which may be a liquid formulation and which may be constituted immediately prior to administration, comprises one or more components that are capable of neutralizing acidic solutions, particularly gastric fluid, for a period of time. The buffer components include, but are not limited to, pharmaceutically acceptable weak acids, weak bases, or mixtures thereof. Preferably, the buffer components are water soluble materials such as phosphoric acid, tartaric acids, lactic acid, succinic acid, citric acid, acetic acid, ascorbic acid, aspartic acid, hydrochloric acid, sulfuric acid, glutamic acid, and salts thereof.

The pharmaceutically acceptable acid neutralizing buffer is administered in an amount sufficient to neutralize gastric fluids in the stomach and increase the amount of the epothilone that is absorbed by the gastrointestinal system. The pharmaceutically acceptable acid neutralizing buffer may be administered as an aqueous solution having a pH of between about 5 to 9. The pharmaceutically acceptable acid neutralizing buffer may be administered as an aqueous solution of anhydrous dibasic sodium phosphate, sodium citrate dihydrate, and anhydrous citric acid.

The present invention increases the bioavailability of the orally administered epothilone significantly above that of an epothilone orally administered without a neutralizing buffer. In one embodiment the bioavailability of the one or more epothilones or a pharmaceutically acceptable salt, solvate, clathrate, hydrate, or prodrug thereof is at least 20 percent. The one or more epothilones or a pharmaceutically acceptable salt, solvate, clathrate, hydrate, or prodrug thereof may be orally administered as a solution in propylene glycol and ethanol, for example, wherein the ratio of propylene glycol:ethanol is about 80:20.

[A preferred epothilone is [1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]heptadecane-5,9-dione.]

*A preferred compound is [1S-[1R*,3R*(E),7R*,10S*,11R*,12R*,16S*]]-7,11-dihydroxy 8,8,10,12,16-pentamethyl-3-[1-methyl-2-(2-methyl-4-thiazolyl)ethenyl-4-aza-17-oxobicyclo[14.1.0]heptadecane-5,9-dione.*

The invention also encompasses kits which comprise the desired epothilone and a soluble buffer composition. The invention encompasses a kit comprising (a) a pharmaceutical composition comprising an epothilone which is suitable for oral administration and (b) a pharmaceutical composition comprising an acid neutralizing buffer which is suitable for oral administration.

In one embodiment the kits include:

(i) a first component comprising one or more epothilones of Formula:

[

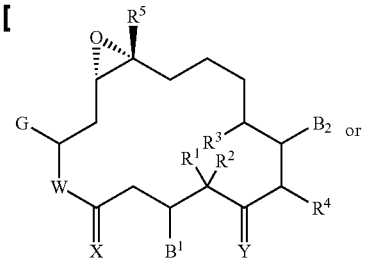

or

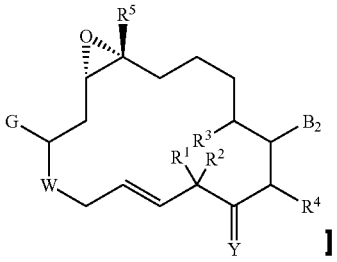

]

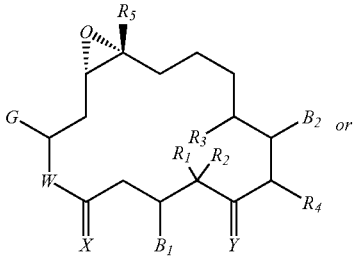

or

-continued

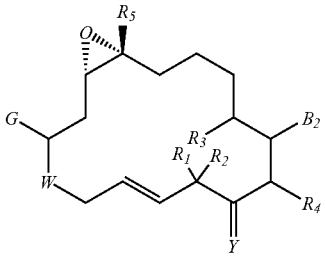

wherein G, W, X, Y, $B_1$, $B_2$, D, $R_1$, $R_2$, $R_3$, $R_4$, $R_5$, $R_8$, $R_9$, $R_{10}$, $R_{11}$, $R_{12}$, $R_{16}$, $R_{17}$, $R_{18}$, $R_{22}$, $R_{23}$, $R_{24}$, $R_{25}$, $R_{26}$, $R_{27}$, [$R_{28}$, $R_{29}$,] $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{51}$, $R_{52}$, *and* $R_{53}$, [and $R_{61}$] are defined above; and (ii) a second component comprising a pharmaceutically acceptable acid neutralizing buffer, wherein the first component and the second component are provided as a liquid oral dosage form or as a solid pharmaceutical composition that can be constituted or reconstituted with a solvent to provide a liquid oral dosage.

The pharmaceutical composition to be reconstituted with a solvent may be provided as a tablet. The first component or the second component may be anhydrous. The kit may optionally include solvents for reconstituting the first or second components. The solvent for reconstituting the first component may be a mixture of propylene glycol and ethanol, wherein the ratio of propylene glycol:ethanol is about 80:20.

The invention is further directed to a pharmaceutical composition comprising:

(i) one or more epothilones of Formula:

[

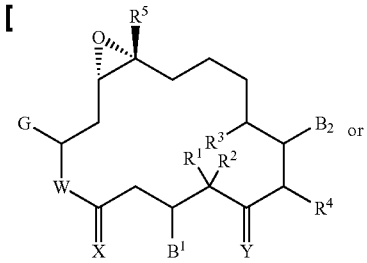

or

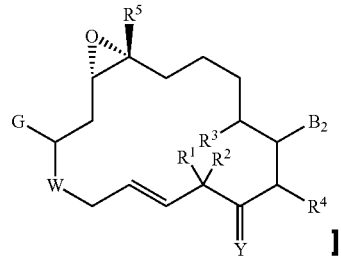

]

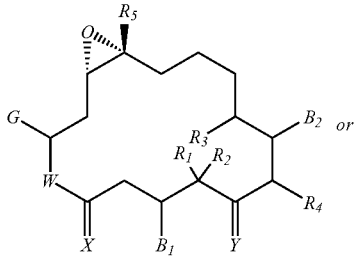

or

-continued

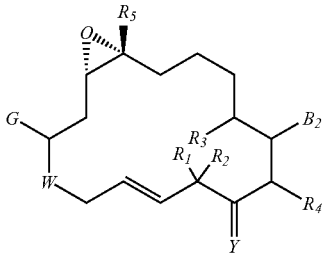

wherein G, W, X, Y, $B_1$, $B_2$, D, $R_1$, $R_2$, $R_3$, $R_4$, $R_5$, $R_8$, $R_9$, $R_{10}$, $R_{11}$, $R_{12}$, $R_{16}$, $R_{17}$, $R_{18}$, $R_{22}$, $R_{23}$, $R_{24}$, $R_{25}$, $R_{26}$, $R_{27}$, [$R_{28}$, $R_{29}$,] $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{51}$, $R_{52}$, *and* $R_{53}$, [and $R_{61}$ ] are defined above, or a pharmaceutically acceptable salt, solvate, clathrate, hydrate or prodrug thereof in solid form; and (ii) a solid pharmaceutically acceptable acid neutralizing buffer in an amount sufficient to reduce decomposition of the one or more epothilones, or a pharmaceutically acceptable salt, solvate, clathrate, hydrate, or prodrug thereof when the pharmaceutical composition is reconstituted with a solvent to provide a liquid oral dosage form.

DETAILED DESCRIPTION OF THE INVENTION

Figure 1:
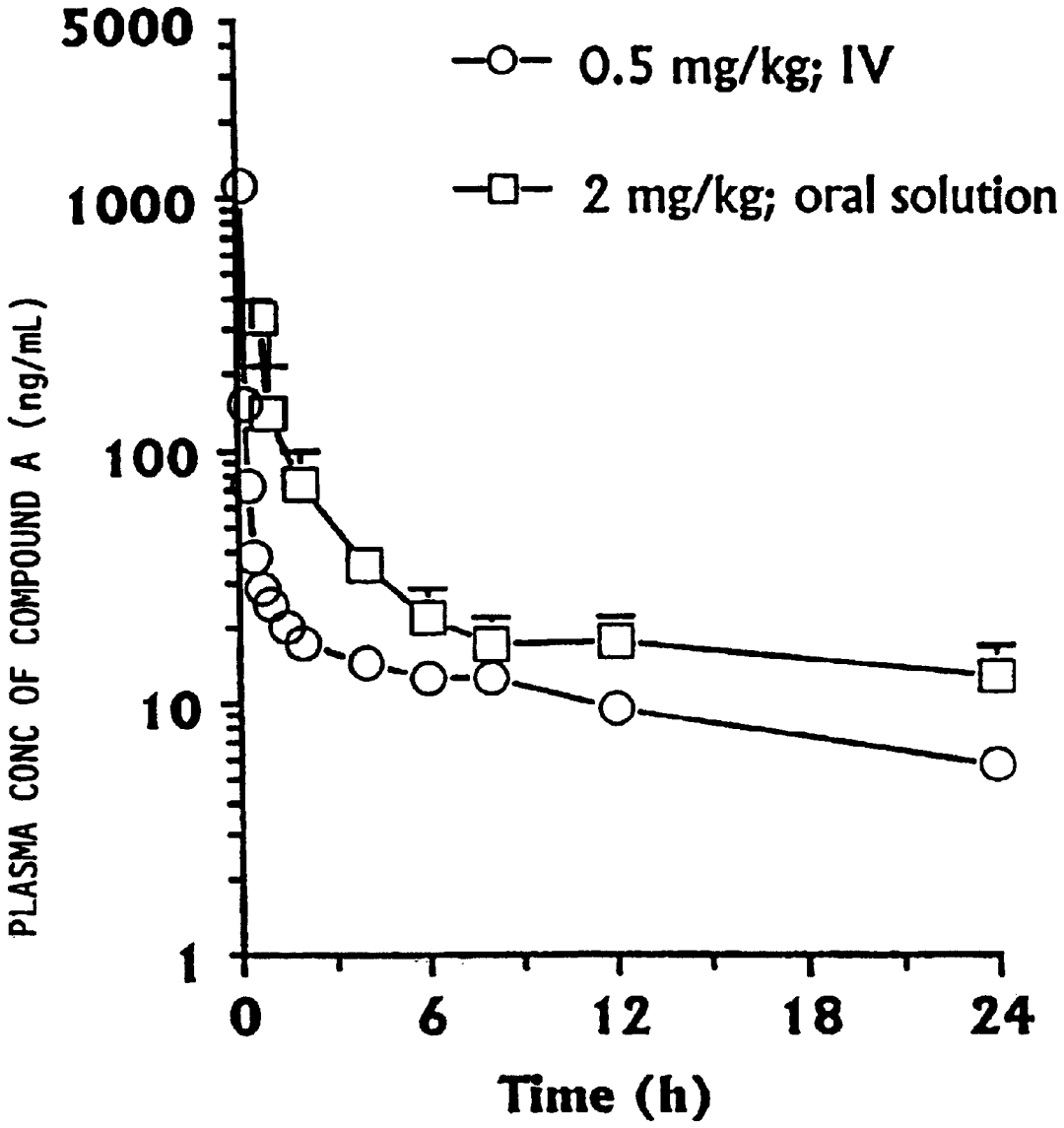
FIG. 1. Mean plasma concentration profiles for Compound (A) vs. time in dogs after IV administration at 0.5 mg/kg, -±-, and oral administration of a 2 mg/kg solution, -□-. Vertical bars represent standard deviations and are shown where larger than the symbol size.

Based upon the pharmacological benefits of epothilones, there is need for dosage forms and methods for administering these compounds so that they are sufficiently bioavailable to have a pharmacological effect. In particular, there is a need for oral dosage forms and more particularly for liquid oral dosage forms that can deliver an amount of epothilone sufficient to treat disease. The present invention is based, in part, on the discovery that epothilones of Formula (Ia) or (Ib):

[

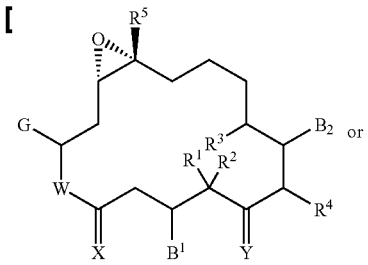

-continued

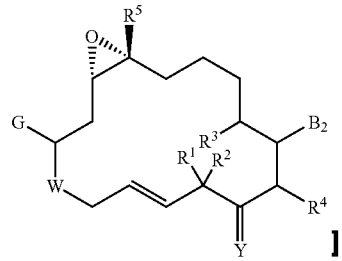

]

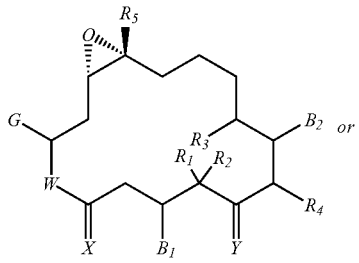

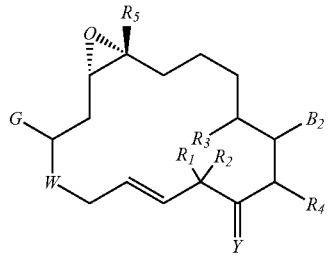

wherein:

G is [selected from the group consisting of] alkyl, substituted alkyl, aryl, substituted aryl, heterocyclo,

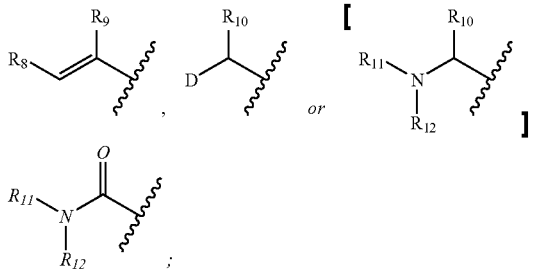

W is O or $NR^{16}$;

X is O; S; $CHR_{17}$; or H, $R_{18}$;

Y is [selected from the group consisting of] O; H, H; H, $OR_{22}$; $OR_{23}$, $OR_{23}$; $NOR_{24}$; H, [$NOR_{25}$] *$NHOR_{25}$*; H, [$HNR_{26}R_{27}$] *$NR_{26}R_{27}$*; [$NHNR_{28}R_{29}$;] H, $NHNR_{30}R_{31}$ or $CHR_{32}$, where $OR_{23}$, $OR_{23}$ can be a cyclic ketal;

$B_1$ and $B_2$ are [selected from the group consisting of] *independently* H, $OR_{33}$, $OCOR_{34}$, $OCONR_{35}R_{36}$, $NR_{37}R_{38}$, or $NR_{39}CONR_{40}R_{41}$ D is [selected from the group consisting of] $NR_{42}R_{43}$ or heterocyclo;

$R_1$, $R_2$, $R_3$, $R_4$, and $R_5$ are [selected from] *independently* H[,] *or* lower alkyl;

$R_8$, $R_9$, $R_{10}$ and $R_{11}$ are [selected from the group consisting of] *independently* H, alkyl, substituted alkyl, aryl, substituted aryl, cycloalkyl, heterocyclo or substituted heterocyclo;

$R_{17}$, $R_{18}$, $R_{22}$, and $R_{23}$ are [selected from the group consisting of] *independently* H, alkyl, [and] *or* substituted alkyl;

$R_{24}$, $R_{25}$, $R_{26}$, [$R_{28}$,] $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{51}$, $R_{52}$, *and* $R_{53}$[, and $R_{61}$ are selected from the group of] *are independently* H, alkyl, substituted alkyl, aryl or substituted aryl;

$R_{12}$, $R_{16}$, $R_{27}$, [$R_{29}$,] $R_{31}$, $R_{38}$, and $R_{43}$, are [selected from the group consisting of] *independently* H, alkyl, substituted alkyl, substituted aryl, cycloalkyl, heterocyclo, $R_{51}C{=}O$, $R_{52}OC{=}O$, $R_{53}SO_2$, hydroxy, [and] O-alkyl or O-substituted alkyl, and pharmaceutically acceptable salts, solvates, hydrates, clathrates or prodrugs thereof, when orally administering in combination with a pharmaceutically acceptable acid neutralizing buffers, are sufficiently bioavailable to have a pharmacological effect. Accordingly, the invention is directed to methods of increasing the bioavailability of orally administered epothilones of Formulae (Ia) or (Ib), or a pharmaceutically acceptable salt, solvate, clathrate, hydrate, or prodrug thereof, by orally administering the one or more epothilones of Formula (Ia) or (Ib), or a pharmaceutically acceptable salt, solvate, clathrate, hydrate, or prodrug thereof, and orally administering a pharmaceutically acceptable acid neutralizing buffer in combination therewith. The invention also relates to pharmaceutical compositions, pharmaceutical dosage forms, and kits for use in the methods of the invention.

A preferred [epothilone] *compound* for use in the methods, compositions, and dosage forms of the invention is [[1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]heptadecane-5,9-dione] [*1S-[1R*,3R*(E),7R*,10S*,11R*,12R*,16S*]]-7,11-dihydroxy 8,8,10,12,16-pentamethyl-3-[1-methyl-2-(2-methyl-4-thiazolyl)ethenyl-4-aza-17-oxobicyclo[14.1.0]heptadecane-5,9-dione*] ("Compound (A)"), depicted below:

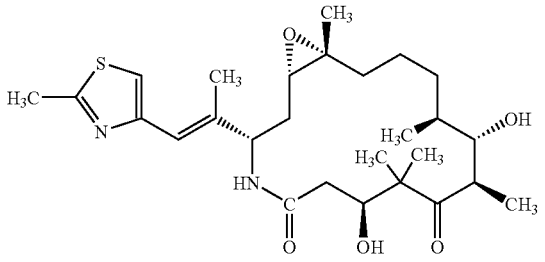

DEFINITIONS

Listed below are definitions of various terms used to describe this invention. These definitions apply to the terms as they are used throughout this specification, unless otherwise indicated in specific instances.

As used herein, the term "alkyl" refers to straight or branched chain unsubstituted hydrocarbon groups of 1 to 20 carbon atoms, preferably 1 to 7 carbon atoms.

As used herein, the term "substituted alkyl" refers to an alkyl group substituted by, for example, one to four substituents, such as, halo, trifluoromethyl, trifluoromethoxy, hydroxy, alkoxy, [cycloalkyoxy] *cycloalkyloxy*, [heterocylooxy] *heterocyclyloxy*, oxo, alkanoyl, aryloxy, alkanoyloxy, amino, alkylamino, arylamino, aralkylamino, cycloalkylamino, [heterocycloamino] *heterocyclylamino*, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, [heterocyclothio] *heterocyclylthio*, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and [heterocyclos] *heterocycles*, such as, indolyl, imidazolyl, furyl, thienyl, thiazolyl, [pyrrolidyl] *pyrrolidinyl*, pyridyl, and pyrimidyl. Where noted above where the substituent is further substituted it will be with halogen, alkyl, alkoxy, aryl or aralkyl.

As used herein, the term "halogen" or "halo" refers to fluorine, chlorine, bromine and iodine.

As used herein, the term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

As used herein, the term "aralkyl" refers to an aryl group bonded directly through an alkyl group, such as benzyl.

As used herein, the term "substituted aryl" refers to an aryl group substituted by, for example, one to four substituents such as alkyl; substituted alkyl, phenyl, substituted phenyl, heterocyclo, halo, trifluoromethoxy, trifluoromethyl, hydroxy, alkoxy, cycloalkyloxy, [heterocyclooxy] *heterocyclyloxy*, alkanoyl, alkanoyloxy, amino, alkylamino, aralkylamino, cycloalkylamino, [heterocycloamino] *heterocyclylamino*, dialkylamino, alkanoylamino, thiol, alkylthio, cycloalkylthio, [heterocyclothio] *heterocyclylthio*, ureido, nitro, cyano, carboxy, carboxyalkyl, carbamyl, alkoxycarbonyl, alkylthiono, arylthiono, alkysulfonyl, sulfonamido, and aryloxy. The substituent may be further substituted by halo, hydroxy, alkyl, alkoxy, aryl, substituted aryl, substituted alkyl or aralkyl.

As used herein, the term "cycloalkyl" refers to optionally substituted, saturated cyclic hydrocarbon ring systems, preferably containing 1 to 3 rings and 3 to 7 carbons per ring which may be further fused with an unsaturated [C3–C7] $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the terms "heterocycle", "heterocyclic" and "heterocyclo" refer to an optionally substituted, fully saturated or unsaturated, aromatic or nonaromatic cyclic group, for example, a 4 to 15 membered system or a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include, but are not limited to, pyrrolidinyl, pyrrolyl, [indolyl,] pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl.

Exemplary bicyclic heterocyclic groups include, but are not limited to, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, *indolyl* indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, and thienothienyl.

Exemplary substituents include, but are not limited to, one or more alkyl groups as described above or one or more groups described above as alkyl substituents. Also included are smaller heterocyclos, such as, epoxides and aziridines.

As used herein, the term "heteroatoms" shall include oxygen, sulfur and nitrogen.

As used herein, the prefix "lower" stands for a moiety having up to and including 7, preferably up to and including 4 carbon atoms.

As used herein, the term "bioavailable" means the extent to which a drug is absorbed into a living system and made available in the circulating blood of the living system. Methods to determine the bioavailability of drugs are well known to those of ordinary skill in the art.

As used herein, the phrase "sufficiently bioavailable to have a pharmacological effect" means that the epothilones are greater than 20 percent bioavailable, preferably greater than 30 percent bioavailable, and more preferably greater than 50 percent bioavailable.

As used herein, the term "pharmaceutically acceptable salt" refers to a salt prepared from an epothilone of Formula (Ia) or (Ib) having a basic functional group, such as an amine, with a pharmaceutically acceptable non-toxic inorganic or organic acid. Suitable non-toxic acids include, but are not limited to, acetic, benzenesulfonic, benzoic, camphorsulfonic, citric, [ethenesulfonic] *ethanesulfonic*, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. Salts formed with acids can be obtained, for example, with an epothilone of Formula (Ia) or (Ib) having a basic functional group and an equivalent amount of a non-toxic acid to provide an acid addition salt. The reaction is typically carried out in a medium in which the acid addition salt precipitates or an aqueous medium followed by evaporation. The term "pharmaceutically acceptable salt" also refers to a salt prepared from an epothilone of Formula (Ia) or (Ib) having an acidic functional group, such as a carboxylic acid functional group, and a pharmaceutically acceptable non-toxic inorganic or organic base. Suitable non-toxic bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like. Salts formed with bases can be obtained, for example, with an epothilone of Formula (Ia) or (Ib) having an acidic functional group and an equivalent amount of a non-toxic base. The reaction is typically carried out in a medium in which the salt precipitates or an aqueous medium followed by evaporation.

The invention also includes zwitterions.

As used herein, the term "pharmaceutically acceptable acid neutralizing buffer" refers to a combination of a pharmaceutically acceptable non-toxic acid and a pharmaceutically acceptable non-toxic salt of an acid that when added to a solution provides a solution that is more resistant to change of pH, compared to a solution without the buffer, when acid or alkali is added to the solution. The term "pharmaceutically acceptable acid neutralizing buffer" also includes compounds, such as basic compounds, that when added to an acidic solution neutralizes the acid and increases the pH of the solution.

As used herein, the term "clathrate" means an inclusion compound formed by the envelopment of a molecule of a "guest" compound in a cage-like hollow space formed by combination of several molecules of a "host" compound.

As used herein, the term "pro-drug" means a derivative of a compound that can hydrolyze, oxidize, or otherwise react under biological conditions (in vitro or in vivo) to provide an epothilone compound of Formula (Ia) or (Ib). For example, carboxylic esters are conveniently formed by esterifying carboxylic acid functionalities; if the epothilone of Formula (Ia) or (Ib) includes an acid functional group it can be esterified to provide a pro-drug. Various pro-drugs are well known in the art (For examples of pro-drugs, see: Design of Prodrugs, edited by H. Bundgaard, Elsevier, 1985; Methods in Enzymology, vol. 42, p. 309–396, edited by K. Widder et al., Academic Press, 1985; A Textbook of Drug Design and Development, edited by Krosgaard-Larsen and H, Bundgaard, chapter 5, "Design and Application of Prodrugs," by H. Bundgaard, p. 113–191, 1991; H. Bundgaard, Advanced Drug Delivery Reviews," 8, 1–38, 1992; H. Bundgaard et al., Journal of Pharmaceutical Sciences, 77, 285, 1988; and N. Kakeya et al., Chem. Phar. Bull., 32, 692, 1984).

As used herein, the phrase "acid neutralization capacity," means the quantity of 1 N HCl (expressed in milliequivalents) that can be brought to pH 3.5, as defined in the U.S. Pharmacopeia, 301.

As used herein, the term "solution" means a liquid preparation that contains one or more soluble active ingredients dissolved in a solvent.

As used herein, the term "suspension" means a finely divided, undissolved active ingredient suspended in a solvent.

As used herein, the term "elixir" means a solution of an active ingredient in a solvent containing water and alcohol.

As used herein, the term "syrup" means a concentrated solution of sugar, such as sucrose, in water or other aqueous liquid, optionally containing polyols, such as glycerin or sorbitol to retard crystallization of the sugar or increase solubility of the added ingredients.

Epothilones Useful in the Methods, Compositions, and Dosage Forms of the Invention Any epothilone can be used in the methods, compositions, and dosage forms of the invention. Preferably, the epothilones are acid labile and poorly soluble in water such that they are not readily bioavailable by the oral route. In a specific embodiment the epothilones of Formula (Ia) or (Ib) are used in the methods, compositions, and dosage forms of the invention. Epothilones of Formula (Ia) or (Ib) can be prepared by the methods disclosed in our co-pending application Ser. No. 09/280,191, filed Mar. 29, 1999 and our co-pending application Ser. No. 09/170,482 filed Oct. 13, 1998, the contents of which are expressly incorporated herein. One of ordinary skill in the art would also recognize that the epothilones of Formula (Ia) or (Ib) could also be prepared by suitable modification of the methodologies disclosed in, for example, K. C. Nicolau et al., "An Approach to Epothilones Based on Olefin Metathesis," Angew. Chem Int. Ed. Engl., 35(20): 2399–2401 (1996); K. C. Nicolau et al., "The Total Synthesis of Epothilone A: The Macrolactonization Approach," Angew. Chem Int. Ed. Engl., 36(5): 525–527 (1997); K. C. Nicolau et al., "Designed Epothilones: Combinatorial Synthesis, Tubulin Assembly Properties, and Cytoxic Action Against Taxol Resistant Tumor Cells," Angew. Chem Int. Ed. Engl., 36(19): 2097–2103 (1997); K. C. Nicolaou et al., "The Olefin Metathesis Approach to Epothilone A and its Analogues", J. Am. Chem. Soc., 119(34): 7960–7973 (1997); K. C. Nicolaou et al., "Total Syntheses of Epothillones A and B via a Macrolactonization-Based Strategy," J. Am. Chem. Soc., 119(34): 7974–7991 (1997); K. C. Nicolaou et al., "Synthesis of Epotilones A and B in Solid and Solution Phase," Nature, 387: 268–272 (1997); and D. Meng et al., "Remote Effects in Macrolide Formation Through Ring-Forming Olefin Metathesis: An Application to the Synthesis of Fully Active Epothilone Congeners," J. Am. Chem. Soc., Vol. 119, No. 11, 2733–2734 (1997).

Preferably, the epothilones are crystalline and anhydrous. Optionally, the epothilones are sterilized before being used in the composition of the invention.

Utility and Uses of the Epothilones or Compositions Thereof

The epothilones of the invention are microtubule-stabilizing agents and, thus, can be used to treat a variety of cancer or other diseases of abnormal cell proliferation. The methods of the invention are particularly useful for administering one or more epothilones of Formula (Ia) or (Ib), or a pharmaceutically acceptable salt, solvate, clathrate, hydrate, or prodrug thereof, to a patient suffering from cancer or other hyperproliferative cellular disease. As used herein, the term "cancer" includes, but is not limited to, solid tumors and blood born tumors. The term cancer refers to disease of skin, tissues, organs, bone, cartilage blood and vessels. The term "cancer" further encompasses primary and metastatic cancers. Examples of cancers that can be treated with the methods of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and [Burketts] *Burkitts* lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, [tetratocarcinoma,] neuroblastoma, and glioma; tumors of the central and peripheral nervous system including, but not limited to, astrocytoma[, neuroblastoma, glioma,] and schwannomas; and other tumors including, but not limited to, [xenoderma,] *xeroderma* pigmentosum, [keratoactanthoma] *keratoacanthoma*, thyroid follicular cancer, and teratocarcinoma.

The methods of the invention are useful for treating patients who have been previously treated for cancer, as well as those who have not previously been treated for cancer. Indeed, the methods and compositions of this invention can be used in first-line and second-line cancer treatments.

The methods of the invention are also useful in combination with known anti-cancer treatments, including radiation. The methods of the invention are especially useful in combination with anti-cancer treatments that involve administering a second drug that acts in a different phase of the cell cycle, e.g., S phase, than the epothilones of Formula (Ia) or (Ib), which exert their effects at the $G_2$-M phase.

Epothilones of Formula (Ia) or (Ib) may also inhibit tumor angiogenesis, thereby affecting abnormal cellular proliferation. Accordingly, the methods of the invention may also be useful in treating certain forms of blindness related to retinal vascularization, arthritis, especially inflammatory arthritis, multiple sclerosis, [restinosis] *restenosis*, and psoriasis.

Epothilones of Formula (Ia) or (Ib) may also induce or inhibit apoptosis, a physiological cell death process critical for normal development and homeostasis. Alterations of apoptotic pathways contribute to the pathogenesis of a variety of human diseases. Accordingly, the methods of the invention will be useful in the treatment of a variety of human diseases with aberrations in apoptosis including cancer (particularly, but not limited to, follicular lymphomas, carcinomas with p53 mutations, hormone dependent tumors of the breast, [prostrate] *prostate* and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus erythematosus, immune mediated glomerulonephritis, rheumatoid arthritis, psoriasis, inflammatory bowel diseases and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

Epothilones of Formula (Ia) or (Ib) may also be formulated or co-administered with other therapeutic agents that are selected for their particular usefulness in administering therapies associates with the aforementioned conditions. For example, each of the compounds of formulae I and II may be formulated with agents to prevent nausea, hypersensitivity, and gastric irritation, such as anti-emetics, and $H_1$ and $H_2$ antihistamines. The above therapeutic agents, when employed in combination with the Epothilones of Formula (Ia) or (Ib), may be used in those amounts indicated in the Physicians' Desk Reference (PDR) or as otherwise determined by one of ordinary skill in the art.

Buffers Useful in the Methods, Compositions, and Dosage Forms of the Invention The purpose of the buffer in the methods of the invention is to temporarily neutralize gastric fluid and thereby reduce degradation of the epothilone in the stomach of the patient. In addition, in aqueous and partially aqueous liquid oral formulations comprising one or more epothilones of Formula (Ia) or (Ib), or a pharmaceutically acceptable salt, solvate, clathrate, hydrate, or prodrug thereof, the buffer reduces decomposition of the epothilone of Formula (Ia) or (Ib). Applicants have surprisingly discovered that liquid oral dosage forms comprising one or more epothilones of Formula (Ia) or (Ib), or a pharmaceutically acceptable salt, solvate, clathrate, hydrate, or prodrug thereof, and a buffer are more stable than a liquid oral dosage form without a buffer.

Buffers useful in the methods, compositions, and dosage forms of the invention may be readily prepared by combining one or more acids and the salt of one or more acids in a ratio such that the combination, when dissolved in an aqueous solution, provides a solution having a pH of between about 5 and 9. Typically, the one or more acids will have a pKa of between about 4 and 10. One of ordinary skill in the art would readily recognize how to prepare buffers that provide a solution having the desired pH value. In addition, the invention contemplates for use as [a] buffer compounds, such as basic compounds, that when added to an acidic solution increase the pH of the solution.

Those skilled in the art would readily recognize a variety of buffers that could be used in the methods, compositions, and dosage forms of the invention. Typical buffers include, but are not limited to pharmaceutically acceptable weak acids, weak bases, or mixtures thereof. Preferably, the buffer components are water soluble materials such as phosphoric acid, tartaric acids, lactic acid, succinic acid, citric acid, acetic acid, ascorbic acid, aspartic acid, glutamic acid, and salts thereof. Preferably, the pharmaceutically acceptable acid neutralizing buffer is a dibasic phosphate-monobasic phosphate buffer or a dibasic phosphate buffer-citric acid-citrate buffer. These buffers are commercially available or can be readily prepared by one of ordinary skill in the art using commercially available buffering agents such as those mentioned above.

Methods of Orally Administering Acid Labile Epothilones of Formula (Ia) or (Ib)

The invention encompasses methods of increasing the bioavailability of orally administered epothilones by orally administering an epothilone of Formula (Ia) or (Ib), or a pharmaceutically acceptable salt, solvate, clathrate, hydrate, or prodrug thereof, and orally administering a pharmaceutically acceptable acid neutralizing buffer. The invention is particularly well suited for epothilones that are acid labile but may also be used with epothilones that are sensitive to hydrolysis under alkaline conditions and for epothilones that are not sensitive to hydrolysis. Further, the invention may be used with epothilones that are poorly soluble in aqueous media.

It should be recognized that the epothilones of the invention can be administered parenterally which would avoid the gastrointestinal system and overcome any bioavailability concerns. However, such administration is inconvenient and uncomfortable for the patient and provides other potential adverse effects. The compositions of this invention and the methods enable the oral route of administration to be used which is a significant advantage, particularly for human patients.

Administering one or more epothilones of Formula (Ia) or (Ib), or a pharmaceutically acceptable salt, solvate, clathrate, hydrate, or prodrug thereof, in combination with a pharmaceutically acceptable acid neutralizing buffer provides increased bioavailability of the one or more epothilones of Formula (Ia) or (Ib). Without being limited by theory, it is believed that the increased bioavailability is due, at least in significant part, to the buffer decreasing the rate of decomposition of the epothilones of Formula (Ia) or (Ib), or a pharmaceutically acceptable salt, solvate, clathrate, hydrate, or prodrug thereof, in the acidic environment of the stomach. Certain epothilones including the preferred epothilone, Compound (A), are unstable in acidic aqueous environments and decompose, presumably by an acid catalyzed hydrolytic opening of the epoxide ring. For example, the time for 5% drug loss ($t_{95}$) at 37° C. for an aqueous solution of Compound (A) is approximately 38 minutes at pH 7.4 but only about 0.2 minutes at pH 2.5. Thus, when epothilones of Formula (Ia) or (Ib), or a pharmaceutically acceptable salt, solvate, clathrate, hydrate, or prodrug thereof, are orally administered they decompose in the stomach of the patient such that they are either minimally absorbed or not absorbed by the gastrointestinal tract.

When one or more epothilones of Formula (Ia) or (Ib), or a pharmaceutically acceptable salt, solvate, clathrate, hydrate, or prodrug thereof, are administered to a patient in combination with a pharmaceutically acceptable acid neutralizing buffer, however, the buffer neutralizes acid in the stomach of the patient so that the rate of decomposition of the one or more epothilones of Formula (Ia) or (Ib), or a pharmaceutically acceptable salt, solvate, clathrate, hydrate, or prodrug thereof is sufficiently decreased so that the one or more epothilones of Formula (Ia) or (Ib), or a pharmaceutically acceptable salt, solvate, clathrate, hydrate, or prodrug thereof remain in the gastrointestinal tract for sufficient time to be absorbed.

In another embodiment of the invention an anti-acid such as hydroxides of aluminum and magnesium; carbonates, such as sodium carbonate and calcium carbonate; silicates; and phosphates can be used to neutralize the acid in the stomach before during or after epothilone administration.

When orally administered according to the methods of the invention, the epothilones of Formula (Ia) or (Ib), or a pharmaceutically acceptable salt, solvate, clathrate, hydrate, or prodrug thereof are at least about 20% bioavailable, preferably at least about 40% bioavailable, and more preferably at least about 50% bioavailable.

In one embodiment of the invention, the one or more epothilones of Formula (Ia) or (Ib), or a pharmaceutically acceptable salt, solvate, clathrate, hydrate, or prodrug thereof and the pharmaceutically acceptable acid neutralizing buffer are provided in a single oral dosage form and are administered simultaneously. The single composition comprising the combination of one or more epothilones of Formula (Ia) or (Ib), or a pharmaceutically acceptable salt, solvate, clathrate, hydrate, or prodrug thereof, and the pharmaceutically acceptable acid neutralizing buffer may be administered as a solid oral dosage form (e.g., a tablet, capsule, or powder) or a liquid oral dosage form (e.g., a solution, suspension, or elixir). The solution or suspension can be constituted just prior to administration using the appropriate solvents or cosolvents to dissolve the epothilone and the buffer components.

For example, the one or more epothilones of Formula (Ia) or (Ib), or a pharmaceutically acceptable salt, solvate, clathrate, hydrate, or prodrug thereof, and the pharmaceutically acceptable acid neutralizing buffer may be administered simultaneously as a solution of the epothilone of Formula (Ia) or (Ib) dissolved in a liquid comprising propylene glycol:ethanol:phosphate buffer (for example at 1M, about pH 8) in a ratio of about 58:12:30, respectively.

In another embodiment of the invention, the epothilone of Formula (Ia) or (Ib) and the pharmaceutically acceptable acid neutralizing buffer are provided as separate distinct pharmaceutical compositions and are administered separately. Each of [which are] *these is* administered as a solid oral dosage form or a liquid oral dosage form.

When the one or more epothilones of Formula (Ia) or (Ib), or a pharmaceutically acceptable salt, solvate, clathrate, hydrate, or prodrug thereof and the pharmaceutically acceptable acid neutralizing buffer are administered separately, the pharmaceutically acceptable acid neutralizing buffer may be orally administered before, after, or both before and after the desired epothilone of Formula (Ia) or (Ib) is administered. Preferably, the pharmaceutically acceptable acid neutralizing buffer is administered both before and after oral administration of the desired epothilone of Formula (Ia) or (Ib), in an amount sufficient to neutralize the stomach acid. When the pharmaceutically acceptable acid neutralizing buffer is administered before the one or more epothilones of Formula (Ia) or (Ib), or a pharmaceutically acceptable salt, solvate, clathrate, hydrate, or prodrug thereof, it is administered within about 5 hours, preferably within about 3 hours, more preferably within about 1 hour, and most preferably within about 10 minutes before the desired epothilone of Formula (Ia) or (Ib) is administered. When the pharmaceutically acceptable acid neutralizing buffer is administered after the desired epothilone of Formula (Ia) or (Ib), or a pharmaceutically acceptable salt, solvate, clathrate, hydrate, or prodrug thereof, it is administered within about 5 hours, preferably within about 3 hours, more preferably within about 1 hour, and most preferably within about 10 minutes before the desired epothilone of Formula (Ia) or (Ib) is administered.

In another embodiment the epothilones of Formula (Ia) or (Ib), or a pharmaceutically acceptable salt, solvate, chlathrate, hydrate, or prodrug thereof, are administered as an enteric coated pill or capsule to delay release of the epothilone until after the pharmaceutically effective acid neutralizing buffer is administered. Enteric coated tablets and capsules are capsules coated with a substances that resist solution in a gastric fluid but disintegrate in the intestine.

In one embodiment the buffer is administered as a dispersible tablet.

The magnitude of the therapeutic dose of the desired epothilone of Formula (Ia) or (Ib), or a pharmaceutically acceptable salt, solvate, clathrate, hydrate, or prodrug thereof, will typically vary with the specific disease and severity of the disease being treated. The dose, and perhaps the dose frequency, may also vary according to age, body weight, response, and the past medical history of the patient. Suitable dosing regimens can be readily selected by those skilled in the art with due consideration of such factors. Typically, the epothilone of Formula (Ia) or (Ib), or a pharmaceutically acceptable salt, solvate, clathrate, hydrate, or prodrug thereof, is orally administered in a total amount of about 0.05 to about 200 mg/kg/day, preferably from about 5 to about 100 mg/kg/day, and more preferably less than about 100 mg/kg/day in a single dose or in about 2 to 4 divided doses.

The invention encompasses pharmaceutical unit dosage forms of the desired epothilone comprising 5 mg/unit, 10 mg/unit, 15 mg/unit, 20 mg/unit, 25 mg/unit, 50 mg/unit, and 100 mg/unit. Similarly, liquid unit doses encompassed by the invention include, but are not limited to, 2.5 mg/mL and 10 mg/mL.

The term "total amount," as used herein, means the combined amount of the epothilones of Formula (Ia) or (Ib), or a pharmaceutically acceptable salt, solvate, clathrate, hydrate, or prodrug thereof, if more than one epothilone of Formula (Ia) or (Ib), or a pharmaceutically acceptable salt, solvate, clathrate, hydrate, or prodrug thereof is in a unit dosage form or administered to the patient Further, the pharmaceutically acceptable acid neutralizing buffer is administered in an amount sufficient to deliver at least about 20 milliequivalents of acid neutralization capacity, preferably at least about 30 milliequivalents of acid neutralization capacity, more preferably at least about 40 milliequivalents of acid neutralization capacity, and most preferably at least about 50 milliequivalents of acid neutralization capacity.

The invention also encompasses pharmaceutical unit dosage forms of the desired buffer comprising about 5 to 100 mg/unit, preferably about 22.5 mg/unit, and more preferably about 22.5 mg/unit. Similarly, liquid unit doses of the buffer encompassed by the invention include about 5 to 100 mg/unit, preferably about 22.5 mg/unit, and more preferably about 22.5 mg/unit dissolved in about 50 to 300 mL of a solvent, preferably about 100 to 200 mL of a solvent, and more preferably about 150 mL of a solvent.

Typically, the pharmaceutically acceptable acid neutralizing buffer is administered as an aqueous solution having a pH of between about 5 to 9, preferably about 6 to 8.5, and more preferably about 7 to 8. Any pharmaceutically acceptable acid neutralizing buffer that provides a solution having a pH in the desired range may be used in the methods of the invention. Preferably, the pharmaceutically acceptable acid neutralizing buffer is a dibasic phosphate-monobasic phosphate buffer or a dibasic phosphate buffer-citric acid-citrate buffer.

In one embodiment of the invention, the patient is first administered the pharmaceutically acceptable acid neutralizing buffer as about 150 mL of an aqueous solution comprising anhydrous dibasic sodium phosphate (about 0.2 M), sodium citrate dihydrate (about 0.07 M), and anhydrous citric acid (about 0.008 M) at a pH of about 7.4; followed by oral administration of one or more epothilones of Formula (Ia) or (Ib), or a pharmaceutically acceptable salt, solvate, clathrate, hydrate, or prodrug thereof as a liquid dosage form in a propylene glycol:ethanol system having a ratio of about 80:20; followed by oral administration of another about 150 mL aqueous solution comprising anhydrous dibasic sodium phosphate (about 0.2 M), sodium citrate dihydrate (about 0.07 M), and anhydrous citric acid (about 0.008 M) at a pH of about 7.4.

Compositions, Unit Dosage Forms, and Kits

The present invention is also directed to kits comprising a first component comprising one or more epothilones of Formula (Ia) or (Ib), or a pharmaceutically acceptable salt, solvate, clathrate, hydrate, or prodrug thereof and a second component comprising a pharmaceutically acceptable acid neutralizing buffer. The first component and the second component are provided as separate distinct pharmaceutical compositions which are intended to be administered separately. The first and second components are provided as a pharmaceutical dosage form suitable for oral administration or as solid pharmaceutical composition that can be constituted or reconstituted with a liquid to provide a liquid oral dosage form. Preferably, the epothilones of Formula (Ia) or (Ib) are packaged in light-protected vials.

Pharmaceutical compositions and dosage forms suitable for oral administration can be presented as discrete dosage forms, such as, but not limited, tablets (e.g., chewable tablets), caplets, capsules, powder in a sachet, enteric coated tablets, enteric coated beads, enteric coated soft gel capsules, and liquids (e.g., flavored syrups). Such dosage forms contain predetermined amounts of the active ingredient and may be prepared by methods of pharmacy well known to those skilled in the art (See Remington's Pharmaceutical Sciences, 18th ed., Mack Publishing, Easton Pa. (1990)).

Typical oral dosage forms are prepared by combining the active ingredients in an intimate admixture with at least one excipient according to conventional pharmaceutical compounding techniques. Excipients can take a wide variety of forms depending on the form of preparation desired for administration. For example, excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents. Examples of excipients suitable for use in oral liquid dosage forms include, but are not limited to, water, glycols, oils, alcohols, flavoring agents, preservation, and coloring agents.

Tablets and capsules represent convenient pharmaceutical compositions and oral dosage forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions and dosage forms of the invention is typically present in from about 50 to about 99 weight percent of the pharmaceutical composition or dosage form.

Disintegrants are used in the pharmaceutical compositions and dosage forms of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form the pharmaceutical compositions and solid oral dosage forms of the invention. The amount of disintegrant used varies based upon the type of formulation, and is readily discernible to those of ordinary skill in the art. Typical pharmaceutical compositions and dosage forms comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The pharmaceutical compositions and dosage forms may further comprise one or more compounds that reduce the rate by which an active ingredient will decompose. Such compounds, which are referred to herein as "stabilizers," include, but are not limited to, antioxidants such as ascorbic acid and salt buffers.

Solutions for oral administration represent another convenient oral dosage form, in which case a solvent is employed. Liquid oral dosage forms are prepared by combining the active ingredient in a suitable solvent to form a solution, suspension, syrup, or elixir of the active ingredient in the liquid.

The solutions, suspensions, syrups, and elixirs may optionally comprise other additives including, but not limited to, glycerin, sorbitol, propylene glycol, sugars, flavoring agents, and stabilizers.

The kits of the invention may include the first and/or second components as an already prepared liquid oral dosage form ready for administration or, alternatively, may include the first and/or second components as a solid pharmaceutical composition that can be reconstituted with a solvent to provide a liquid oral dosage form. When the kit includes the first and/or second components as a solid pharmaceutical composition that can be reconstituted with a solvent to provide a liquid oral dosage form, the kit may optionally include the reconstituting solvent.

The constituting or reconstituting solvent is combined with the active ingredient to provide a liquid oral dosage form of the active ingredient. Preferably, the active ingredient is soluble in the solvent and forms a solution. The solvent may be water, a non-aqueous liquid, or a combination of a non-aqueous component and an aqueous component. Suitable non-aqueous components include, but are not limited to oils; alcohols, such as ethanol; glycerin; and glycols, such as polyethylene glycol and propylene glycol.

The pharmaceutically acceptable acid neutralizing buffers of the invention are preferably water soluble. Accordingly, the preferred solvent for the pharmaceutically acceptable acid neutralizing buffers is water or water based systems including saline solutions or dextrose solutions.

Epothilones of Formula (Ia) or (Ib), or a pharmaceutically acceptable salt, solvate, clathrate, hydrate, or prodrug thereof are relatively insoluble in water. Accordingly, for epothilones of Formula (Ia) or (Ib), or a pharmaceutically acceptable salt, solvate, clathrate, hydrate, or prodrug thereof, non-aqueous liquids or liquids that are a combination of a miscible aqueous component and a non-aqueous component are preferred with non-aqueous liquids being most preferred.

A preferred non-aqueous liquid for epothilones of Formula (Ia) or (Ib), or a pharmaceutically acceptable salt, solvate, clathrate, hydrate, or prodrug thereof is surfactant such as propylene glycol and ethanol, preferably in a ratio of about 80:20. Suitable non-aqueous liquids or surfactants include, but are not limited to, polyethylene glycol, polysorbates, propylene glycol, glyceryl esters, Cremophor, fatty acid esters and alcohols, polyoxyethylene, and fatty alcohol esters and ethers.

When the solvent for the epothilones of Formula (Ia) or (Ib), or a pharmaceutically acceptable salt, solvate, clathrate, hydrate, or prodrug thereof, includes an aqueous component, it is preferred that the aqueous component is buffered to reduce decomposition of the epothilone of Formula (Ia) or (Ib). Liquid oral dosage forms comprising one or more epothilones of Formula (Ia) or (Ib), or a pharmaceutically acceptable salt, solvate, clathrate, hydrate, or prodrug thereof, in an aqueous or partially aqueous solvent [provides] *provide* liquid oral dosage forms that are more stable than a liquid oral dosage form without a buffer. Specifically, it has been discovered that the rate of decomposition of one or more epothilones of Formula (Ia) or (Ib), or a pharmaceutically acceptable salt, solvate, clathrate, hydrate, or prodrug thereof, in a buffered liquid oral formulation is less than the rate of decomposition in an unbuffered liquid oral formulation. Without wishing to be bound by theory, it is believed that epothilones of Formula (Ia) or (Ib) are unstable in acidic and basic medium, presumably as a result of an acid or base catalyzed hydrolytic opening of the epoxide ring. By buffering the liquid oral formulation, however, it is possible to maintain the pH of the liquid oral formulation at a value such the rate of decomposition of the epothilone of Formula (Ia) or (b) is slow enough that the epothilone of Formula (Ia) or (Ib) does not decompose before it can be administered to a patient. The aqueous or partially aqueous liquid oral dosage forms are preferably buffered to a pH of between about 5 to 9, preferably about 6 to 8.5, and more preferably about 7 to 8.

When the active ingredient is provided as a solid pharmaceutical composition that is constituted or reconstituted with a solvent to provide a liquid oral dosage form it is typically provided in powdered form and constituted with the liquid shortly before administration to the patient. The powdered pharmaceutical composition may be packaged, for example, in a vial to which is added the solvent. Alternatively, the contents of the vial may be added to the solvent in a separate container. The powdered active ingredient of the invention may also be packaged in a sachet, such as a foil package, that can be opened and the contents added to the solvent. The powdered active ingredient of the invention may also be formulated as a tablet that dissolves when it is added to the solvent. Often the tablet includes a disintegrant to facilitate dissolution of the tablet.

The present invention is also directed to pharmaceutical compositions comprising one or more epothilones of Formula (Ia) or (Ib), or a pharmaceutically acceptable salt, solvate, clathrate, hydrate, or prodrug thereof, in solid form and a solid pharmaceutically acceptable acid neutralizing buffer in an amount sufficient to reduce decomposition of the one or more epothilones of Formula (Ia) or (Ib), or a pharmaceutically acceptable salt, solvate, clathrate, hydrate, or prodrug thereof, when the pharmaceutical composition is reconstituted with a liquid to provide a liquid oral dosage form.

In addition to providing a more stable liquid oral dosage form, the pharmaceutical compositions of the invention also provide a liquid oral dosage form wherein the epothilone is more bioavailable when orally administered to a patient. Accordingly, the invention is also directed to a liquid oral dosage form comprising one or more epothilones of Formula (Ia) or (Ib), or a pharmaceutically acceptable salt, solvate, clathrate, hydrate, or prodrug thereof, and a solid pharmaceutically acceptable acid neutralizing buffer dissolved in or dispersed in a solvent. Preferably, the one or more epothilones of Formula (Ia) or (Ib), or a pharmaceutically acceptable salt, solvate, clathrate, hydrate, or prodrug thereof, and the solid pharmaceutically acceptable acid neutralizing buffer are dissolved in the liquid to provide a solution.

Preferably, the buffer is present in the pharmaceutical composition such that it provides a liquid oral formulation having a pH of between about 5 to 9, preferably about 6 to 8.5, and more preferably about 7 to 8. Typically, the pharmaceutically acceptable acid neutralizing buffer is present in an amount sufficient to deliver at least about 20 milliequivalents of acid neutralization capacity, preferably at least about 30 milliequivalents of acid neutralization capacity, more preferably at least about 40 milliequivalents of acid neutralization capacity, and most preferably at least about 50 milliequivalents of acid neutralization capacity when reconstituted with a liquid to provide the liquid oral dosage form. Any pharmaceutically acceptable acid neutralizing buffer that can provide a pH within this range may be used in the composition of the invention. Preferably, the pharmaceutically acceptable acid neutralizing buffer is a dibasic phosphate-monobasic phosphate buffer or a dibasic phosphate buffer-citric acid-citrate buffer.

Typically, the pharmaceutical compositions of the invention comprise the one or more epothilones of Formula (Ia) or (Ib), or a pharmaceutically acceptable salt, solvate, clathrate, hydrate, or prodrug thereof, in a total amount of about 0.05 to about 200 mg, preferably from about 5 to about 100 mg, and more preferably about 10 to 50 mg.

The invention further relates to a kit comprising a pharmaceutical composition comprising (i) a combination of one or more epothilones of Formula (Ia) or (Ib), or a pharmaceutically acceptable salt, solvate, clathrate, hydrate, or prodrug thereof, in solid form and a solid pharmaceutically acceptable acid neutralizing buffer and (ii) a solvent for reconstituting the pharmaceutical composition to provide a liquid oral dosage form, wherein the pharmaceutically acceptable acid neutralizing buffer is present in an amount sufficient to reduce decomposition of the one or more epothilones of Formula (Ia) or (Ib), or a pharmaceutically acceptable salt, solvate, clathrate, hydrate, or prodrug thereof, when the combination is reconstituted with the solvent to provide the liquid oral dosage form.

The reconstituting solvent is combined with the active ingredient to provide a liquid oral dosage form of the active ingredient. The liquid oral dosage form may be a solution or a suspension. Preferably, the active ingredient is soluble in the solvent and forms a solution. The solvent may be water, a non-aqueous liquid, or a liquid that is a combination of a non-aqueous component and an aqueous component. Suitable non-aqueous components include, but are not limited to oils; alcohols, such as ethanol; glycerin; and glycols, such as polyethylene glycol and propylene glycol. A suitable solvent for use in the kit of the invention is propylene glycol:ethanol:phosphate buffer (1M, pH 8) in a ratio of about 58:12:30.

The solvent may further comprise one or more additional additives such as, but not limited to, glycerin, sorbitol, propylene glycol, flavoring agents, and preservatives to improve the palatability of the liquid oral dosage form.

This invention further encompasses anhydrous pharmaceutical compositions and dosage forms comprising the active ingredients, i.e., the one or more epothilones of Formula (Ia) or (Ib), or a pharmaceutically acceptable salts, solvate, clathrate, hydrate, or prodrug thereof and/or the pharmaceutically acceptable acid neutralizing buffer. Anhydrous pharmaceutical compositions and dosage forms are advantageous since water can facilitate the degradation of some compounds. For example, the addition of water (e.g., 5%) is widely accepted in the pharmaceutical arts as a means of simulating long-term storage in order to determine characteristics such as shelf-life or the stability of formulations over time (See, e.g., Jens T. Carstensen, Drug Stability: Principles & Practice, 2d. Ed., Marcel Dekker, NY, N.Y., 1995, pp. 379–80). In effect, water and heat accelerate the decomposition of some compounds. Thus, the effect of water on a formulation can be of great significance since moisture and/or humidity are commonly encountered during manufacture, handling, packaging, storage, shipment, and use of formulations. Anhydrous pharmaceutical compositions and dosage forms are especially advantageous for pharmaceutical compositions and dosage forms comprising one or more epothilones of Formula (Ia) or (Ib), or a pharmaceutically acceptable salt, solvate, clathrate, hydrate, or prodrug thereof, since these compounds are sensitive to moisture.

Anhydrous pharmaceutical compositions and dosage forms should be prepared and stored such that its anhydrous nature is maintained. Anhydrous pharmaceutical compositions and dosage forms of the invention can be prepared using anhydrous or low moisture containing ingredients and low moisture or low humidity conditions. Anhydrous pharmaceutical compositions and dosage forms are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

EXAMPLES

Certain embodiments of the invention, as well as certain advantages of the invention, are illustrated by the following non-limiting examples.

Example 1

Pharmacokinetic and Pharmacodynamic Studies of Compound (A) in Mice, Rats, and Dogs 1.1 Sample Analysis Plasma samples from pharmacokinetic/pharmacodynamic studies were analyzed for the concentration of Compound (A) using an LC/MS/MS (liquid chromatography/mass spectrometry/mass spectrometry) assay with a standard curve range of 5 to 20,000 ng/mL (10 to 40,000 nM) for studies in mice and 2 to 1000 ng/mL (4 to 2000 nM) for studies in rats and dogs. In pharmacodynamic studies, concentrations of Compound (A) were determined using the LC/MS/MS assay with a standard curve range of 5 to 20,000 ng/mL (10 to 40,000 nM) in mouse plasma. The LC/MS/MS assay was also used to determine the concentrations of Compound (B), a degradation product of Compound (A) formed in the stock/dosing solution or in vivo, in rat and dog plasma. The structure of Compound (B) is:

Compound (B)

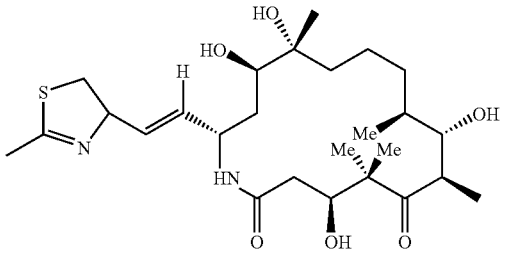

Samples were analyzed by adding an internal standard to 0.2 mL of sample, precipitating with acetone, and then extracting the supernatant with 1-chlorobutane. The organic layer was removed and evaporated to dryness. The residue was reconstituted and injected into the LC/MS/MS system. For human plasma, chromatrographic separation was achieved, isocratically, on a YMC ODS-AQ column (4.6×50 mm, 3 mm) with a mobile phase of acetonitrile:0.01M ammonium acetate, pH 5.0 (65:35). For dog plasma, chromatographic separation was achieved, isocratically, on a Zorbax Stable Bond C18 column (2.1×150 mm, 5 mm) maintained at 40EC with a mobile phase of 0.1M ammonium acetate pH 5 and acetonitrile. For rat plasma, chromatographic separation was achieved, isocratically, on a Stable Bond C18 column (2.1×150 mm, 5 mm) maintained at 40EC with a mobile phase of acetonitrile:0.1M ammonium acetate, pH 5.0 (1:1). Detection was by negative electrospray tandem mass spectrometry. The standard curve, which ranged from 2 to 500 ng/mL for all analytes and was fitted to a 1/×weighted quadratic regression model.

Compound (A) and Compound (B) were found to be stable at room temperature for at least 4 h in rat and dog EDTA (ethylenediaminetetraacetic acid) plasma prior to processing for analytical work and for at least 24 h at 4° C. in an autosampler after processing, and for at least 5 weeks at −20° C. or lower in rat and dog plasma, and through at least 3 freeze-thaw cycles. In addition, both analytes were also found to be stable in fresh rat and dog EDTA whole blood at room temperature for at least 0.5 h.

1.2 Pharmacokinetics in Mice

Compound (A) was administered intravenously (5 mg/kg) and orally (48 mg/kg) to female CDF, mice. For the IV route, Compound (A) was dissolved in 20% ethanol solution and was given as a bolus dose. For the oral route, solutions of Compound (A) were prepared as a 3:7 mixture of ethanol-:phosphate buffered saline (0.25 M, pH 8.0) and administered by gavage. Plasma samples for determinating concentrations of Compound (A) were taken from 3 separate mice at 5, 15, and 45 min, and 2, 4, and 6 h after the IV dose, and at 15 and 45 min, and 2, 4, and 6 h after the oral dose.

After IV administration, the systemic clearance or total body clearance (CLT) of Compound (A) was 68 mL/min/kg and represented 76% of the liver blood flow (90 mL/min/kg) and the steady-state volume of distribution (VSS) of 6.3 L/kg suggested extensive extravascular distribution, since the total body water in mice is approximately 0.7 L/kg (See, B. Davies and T. Morris, Physiological Parameters in Laboratory Animals and Humans," Pharmaceutical Research, 1993, 10(7), 1093–1095). The terminal elimination half-life (T-HALF) was approximately 3 h.

After oral administration of Compound (A), the peak plasma concentration (CMAX) was 5983 ng/mL and the time to reach CMAX (TMAX) was achieved at 0.25 h postdose, suggesting that the absorption of Compound (A) was rapid. The absolute oral bioavailability of Compound (A) was 31%.

1.3 Pharmacokinetics in Rats

Compound (A) was given as a single intraarterial (2 mg/kg; 10 min infusion), oral (8 mg/kg), and intraduodenal (8 mg/kg) dose to fasted male Sprague Dawley rats (n×3–6 per group). All dosing solutions were prepared in 20% ethanol. Plasma samples were obtained over a period of 24 h after dosing and the concentration of Compound (A) was determined using the LC/MS/MS assay.

After intraarterial administration, the plasma concentration-time profiles exhibited biphasic disposition with a rapid decline until 2 h postdose and a slow terminal phase. The CLT (mean value=56 mL/min/kg) of Compound (A) represented 100% of the liver blood flow (56 mL/min/kg), and the VSS (mean value=23 L/kg) was suggestive of extensive extravascular distribution, since the total body water in rats is about 0.7 L/kg (See, B. Davies and T. Morris, Physiological Parameters in Laboratory Animals and Humans," Pharmaceutical Research, 1993; 10 (7), 1093–1095). The mean T-HALF value was 9.6 h.

After oral and intraduodenal administration, mean CMAX values were 228 and 642 ng/mL, respectively; TMAX values were 0.17 h and 0.08 h, respectively, suggesting that the absorption of Compound (A) was rapid. The absolute oral bioavailability of Compound (A) after oral and intraduodenal administration in the rat was 7.5% and 27%, respectively.

In another study, bile duct cannulated Sprague Dawley rats (n=2 per group) received a single intraterial (10 mg/kg) or oral (20 mg/kg) dose of Compound (A), and bile, urine, and plasma samples were collected over a period of 9 h after dose. There was negligible excretion of intact Compound (A) in the bile (C 1% of the dose). There was some detectable amount of Compound (A) in the urine, but actual concentrations were not quantified due to lack of stability data for Compound (A) in the urine. Several drug-related compounds in the urine and plasma were tentatively identified by LC/MS and included an isomer (M+0), and a hydrolysis product (M+18). In addition, a metabolite (M−2) was detected in the plasma.

1.4 Pharmacokinetics in Dogs

Male beagle dogs (n=3) were administered a 10 min IV infusion of 0.5 mg/kg of Compound (A) (given as a 10% ethanol solution). Plasma samples were taken over a period of 32 h after dose to determine the plasma concentrations of Compound (A). The plasma concentration-time curve displayed a multiphase profile, with an initial rapid decline in Us concentration over 2 hour after dose and a slow terminal elimination phase. The CLT (mean value=17.3 mL/min/kg) of Compound (A) represented about 56% of the liver blood flow (30.9 mL/min/kg) and the means VSS of 25.2 L/kg suggested extensive extravascular distribution based on the total body water of 0.6 L/kg in dogs. The T-HALF was estimated to be approximately 24 h.

The kinetics of Compound (A) were also evaluated as part of a single dose IV toxicology study. Compound (A) was given as an IV infusion (ca. 15 min) at doses of 0.5 and 5 mg/kg to 2 dogs/gender/dose. Dosing solutions of Compound (A) were prepared in 40% propylene glycol, 5% Cremophor EL®, 5% ethanol, and 50% phosphate buffer (50 mM, pH 7.4) the day prior to dosing. Blood samples were obtained over a period of 48 h after dosing, and plasma concentrations of Compound (A) and Compound (B) were determined using the LC/MS/MS assay with a standard curve range of 2–500 ng/mL for both analytes. For doses of 0.5 and 5 mg/kg of Compound (A), the mean CMAX values for Compound (A), combined across gender, were 218 and 5118 ng/mL, respectively, and the mean AUC values were 316 and 6925 h.ng/mL, respectively. For doses in a ratio of 1:10, the means CMAX and AUC values of Compound (A) were in the ratio of 1:23 and 1:27, respectively, suggesting that the kinetics of Compound (A) were nonlinear between 0.5 and 5 mg/kg doses. T-HALF, MRT(INF), CLT, and VSS were not determined due to the limited sampling used in the study.

For Compound (B), the mean CMAX values were 95.6 and 984 ng/nL for the 0.5 and 5 mg/kg dose groups, respectively, and the mean AUC values were 55.0 and 1109 h.ng/mL, respectively. The mean CMAX and AUC values for Compound (B) were in the ratio of 1:10 and 1:20, respectively. Gender effect on the kinetics of Compound (A) could not be conclusively evaluated due to a small sample size, but the kinetics appeared to be reasonably similar between gender.

This study shows that a dose related increase in the systemic exposure to Compound (A) is observed with the increase being more than proportional to the increase in dose. Furthermore, dose-related increase in the systemic exposure to Compound (B) was also observed.

Example 2

Toxicokinetics in Rats

The toxicokinetics of Compound (A) were evaluated in a single dose IV toxicology study in rats. Dosing solutions of Compound (A) were prepared in 50% propylene glycol, 10% Cremophor EL, 10% ethanol, and 30% phosphate buffer (50 mM, pH 7.4) the day prior to dosing. Compound (A) was given as an IV infusion (ca. 3 min) at doses of 10, 25, and 30 mg/kg to 3 rats/gender/dose. Serial blood samples were obtained over a period of 24 h after dosing, and plasma concentrations of Compound (A) and Compound (B) were determined using an LC/MS/MS assay with a standard curve range of 2–500 ng/mL for both analytes. At a dose of 10, 25, and 30 mg/kg, the mean CMAX values of Compound (A) in male rats were 6422, 19066, and 24414 ng/mL, respectively; in female rats, the mean CMAX values were 8384, 20524, and 25054 ng/mL, respectively. The mean values for the area under the concentration vs. time curve (AUC) for the 10, 25, and 30 mg/kg dose group were 3864, 11980, and 19269 h.ng/mL in male rats, respectively; in female rats, the values were 8156, 28476, and 34563 h.ng/mL, respectively. For doses in a ratio of 1:2.5:3 proportion, the mean CMAX values of Compound (A) for males and females were in the ratio of 1:3.0:3.8 and 1:2.5:3.0, respectively, and the AUC values were in the ratio of 1:3.1:4.9 and 1:3.5:4.2, respectively. T-HALF, mean residence time over the time interval zero to infinity MRT(INF), total body clearance (CLT), and VSS were not determined due to the limited sampling used in the study.

For Compound (B), the CMAX and AUC values across gender and dose groups ranged between 499 to 1787 ng/nt and 222 to 2003 h.ng/mL, respectively. The CMAX values for Compound (B) in males and females were in the ratio of 1:2.6:3.6 and 1:3.0:2.8, respectively, and the AUC values were in the ratio of 1:3.4:7.0 and 1:4.3:5.5, respectively. AUC values of Compound (A) and Compound (B) were higher by 1.8 to 2.4-fold and 1.3 to 2.0-fold, respectively, in female rats compared to male rats.

This study shows that there is a dose-related increase in systemic exposure to Compound (A) with the increase being more than proportional to the increase in dose, with females having higher exposure than male rats. Furthermore, dose-related increase in the systemic exposure to Compound (B) was also observed.

Example 3

Pharmacodynamic Studies of Compound (A)

A series of experiments were conducted to evaluate the anticancer activity of Compound (A) administered as an IV infusion over a period of 10 h in nude female mice bearing subcutaneous human ovarian carcinoma (Pat-7 tumor). Compound (A), as a solution in 10% ethanol, was administered at doses of 3 to 150 mg/kg. Results from these experiments suggested that a dose between 3 to 6 mg/kg of Compound (A) was considered to be a minimum effective dose (defined as a dose required to produce activity equivalent to 0.5 log cell kill). In a series of parallel experiments, the apparent steady-state concentrations of Compound (A) was determined in mice after 10 h IV infusion doses of 3 to 150 mg/kg. Plasma concentrations of Compound (A) were determined at 2, 4, and 6 h after the start of the infusion, and were comparable for each dose level across time points suggesting that steady-state was reached by 2 h. Therefore, the concentrations at 2, 4, and 6 h were averaged to determine an apparent steady-state concentration. Dose-related increases in the apparent steady-state concentration were observed over the entire dose range of 3 to 150 mg/kg. The minimum effective concentration, defined as the apparent steady-state concentration achieved by the minimum effective IV infusion dose between 3 to 6 mg/kg, was observed to be between 15 to 45 ng/nL (ca. 30 to 90 nM).

Example 4

In Vitro Studies on the Metabolism of Compound (A)

Upon incubation of Compound (A) (40 :M) with mouse, rat, dog, and human liver microsomes fortified with nicotinamide adenine dinucleotide phosphate (NADPH), the rate of oxidative metabolism of Compound (A) was 2.1, 0.7, 1.2 and 1.3 nmol/min/mg protein, respectively. Moreover, the metabolite distribution was similar among all species (metabolite masses included several M+6 and M−2 compounds). Qualitatively, there appeared to be similar production of metabolites of Compound (A) after incubation with rat or human hepatocytes compared to microsomal incubations. Products similar to those arising from the chemical degradation of Compound (A) appeared to be the major products in the hepatocyte incubations.

The ability of Compound (A) to inhibit the major human cytochrome P450s (CYPs) responsible for the metabolism of drugs was evaluated in vitro using recombinant human CYP isoforms. $IC_{50}$ values for inhibition of deethylation of 3-cyano-7-ethoxycoumarin (CYP1A2, CYP2C9, CYP2C19, and CYP2D6) and for inhibition of dealkylation of benzoylresorufin (CYP3A4) were determined. Compound (A) was a weak inhibitor of human CYP3A4 with an average $IC_{50}$ value of 7.3 p.M (3.7 p.g/mL). The compound did not inhibit CYP1A2, CYP2C9, CYP2C19, and CYP2D6. These in vitro results suggest that Compound (A) may have minimal potential to alter the metabolic clearance of drugs that are highly metabolized by CYP3A4, and is unlikely to significantly alter the metabolic clearance of drugs metabolized by CYP1A2, CYP2C9, CYP2C19, and CYP2D6.

Compound (A) was incubated with human liver microsomes along with compounds specific for the inhibition of individual cytochrome P450s commonly involved in drug metabolism. The inhibitors used were ; furafylline (CYPIA2), 8-methoxypsoralen (CYP2A6), orphenadrine (CYP2B6), sulfaphenazole (CYP2C9), tranylcypromine (CYP2C19), quinidine (CYP2D6), troleandomycin (CYP3A4), and ketoconazole (CYP3A4). Significant inhibition was observed only with the CYP3A4 inhibitors, both of which completely inhibited the biotransformation of Compound (A). Thus, in humans, Compound (A) may be a substrate for CYP3A4.

The permeability coefficient (Pc) of Compound (A) was studied in the Caco-2 cell culture system, an in vitro model for human intestinal absorption. The Pc of Compound (A) at 10, 30, and 100 pM (Ca 5, 15, and 50 pg/mL, respectively) concentration was 94, 105, and 128 nm/sec, respectively. The Pc of some model compounds, for which the bioavailability in humans is known, was also determined in the same experiment. These compounds included salicylic acid, acetaminophen, ibuprofen, and propranolol, all of which had Pc>200 nm/sec and are at least 90% absorbed. The Pc values of 94–128 nm/sec for Compound (A) suggests that Compound (A) has the potential for good absorption in humans.

Example 5

Pharmacokinetics and Absolute Oral Bioavailability of Various Formulations of Compound (A) in Beagle Dogs The absolute oral bioavailability of various formulations of Compound (A) in adult male beagle dogs (n=4) was evaluated. Compound (A) was given as a 10 min intravenous (IV) infusion (0.5 mg/kg), a buffered oral solution (2 mg/kg), and a buffered oral suspension (1 mg/kg).

5.1 Experimental Design

The experimental design for the study is given in Table 1.

TABLE 1

Experimental Design

| Period | Treat-ment | Route | Dose (mg/kg) | Formulation | No. of dogs |
|---|---|---|---|---|---|
| 1 | A | IV | 0.5 | Solution in 40% propylene glycol, 5% ethanol, and 55% phosphate buffer (50 mM, pH-7.4) | 4 |
| 2 | B | Oral | 2 | Solution in 58% propylene glycol, 12% ethanol, and 30% phosphate buffer (1 M, pH 8.0) | 4 |
| 3 | C | Oral | 2[a] | Buffered suspension in 1% Avicel ® RC591 containing phosphate buffer (2 M, pH 8.0) and citric acid (85 mM). | 4 |
| 4 | D | Oral | 2 | n.a.[d] | n.a.[d] |

[a]Due to toxicity this dose was reduced to 1 mg/kg.
[b]Treated 15 min prior to dosing with pentagastrin (6:g/kg; intramuscularly).
[c]This treatment was not administered due to lack of an evaluable formulation.
[d]Not Applicable.

The design was a single-dose, four-treatment, four-period, non-randomized, crossover design. Compound (A) was given to four adult male beagle dogs as a 10 min IV infusion (0.5 mg/kg), a buffered oral solution (2 mg/kg), or a buffered oral suspension (2 mg/kg). For IV administration, Compound (A) was formulated as a solution (about 0.375 mg/mL strength) in 40% propylene glycol, 5% ethanol, and 55% phosphate buffer (50 mM, pH=7.4). The oral solution of Compound (A) (about 1.5 mg/mL strength) was prepared in 58% propylene glycol, 12% ethanol, and 30% phosphate buffer (1 M, pH 8.0) as the vehicle. For the oral suspension, Compound (A) was suspended in 1% Avicel® RCS91 which contained phosphate buffer (2 M) and citric acid (85 mM). Upon reconstitution, the pH of the buffered suspension was about 8.0 and the strength was approximately 0.75 mg/mL. Due to cumulative toxicity the dose for the oral suspension scheduled during the third treatment period was reduced from 2 mg/kg to 1 mg/kg. Furthermore, the fourth treatment was not administered for lack of an evaluable formulation. The wash-out period between treatments was at least 7 days. Serial blood samples were collected over 24 h after dose administration and concentrations of Compound (A) and Compound (B) were determined using a LC/MS/MS assay with a standard curve range of 2–500 ng/mL for both analytes. The LC/MS/MS assay was the same as used in Example 1.

Analytical runs consisted of standard, quality control (QC), and study samples. The plasma volume used for analysis was 0.2 mL and the standard curve range was 2 to 500 ng/mL for both analytes, defining the lower limit of quantitation (LLQ) and upper-limit of quantitation (ULQ), respectively. If the predicted concentration of a study sample was less than that of the lowest standard, the value of the predicted concentration was reported as <LLQ. If the predicted concentration was reported as <LLQ. If the predicted concentration was greater than that of the highest standard, the result of that analysis was reported as >ULQ and an appropriate volume of that sample was diluted with blank plasma and reanalyzed.

5.2 Animal Preparation, Handling, and Dose Administration

Four adult male dogs with venous access for drug administration and blood collection were selected for the study. The dogs were acclimated for at least one week prior to study initiation and were housed in individual steel cages. Animals were identified by a unique number and by a tag attached to the cage. The dogs were offered drinking water ad libitum, and fed once a day with standard canine diet except for an overnight (about 12 h) fast prior to dosing which was continued until 4 h after dosing. Fifteen (15) minutes prior to administration of the buffered oral suspension, the dogs were pretreated with pentagastrin (6 :g/kg; intramuscularly). Pentagastrmn pretreatment was used only for the oral suspension leg. The IV dose was administered as a constant-rate infusion over a period of 10 min using a calibrated infusion pump. The oral solution and suspension doses were administered by gavage and the gavage tubes were rinsed with 20 mL of water.

5.3 Sample Collection and Handling

Serial blood samples (3 mL) were collected at predose, and 10 min (IV only; end-of-infusion), 15 min, 20 min (IV only), 30 min, and 45 min, and 1 h, 1.5 h, 2 h, 4 h, 6 h, 8 h, 12 h, and 24 h after dosing. Blood samples were collected into Vacutainer® tubes containing $K_3$-EDTA as the anticoagulant and the contents of each tube were mixed by gently inverting the tube. The blood samples were then placed immediately on chipped ice. Plasma was obtained within 30 min of collection by centrifuging the tubes at approximately 4° C. and 2000×g for 5 min. Plasma samples were stored at or below −20° C. until analyzed for the concentrations Compound (A) and Compound (B).

The following acceptance criteria were applied a priori to each analytical run for the analysis of Compound (A) and Compound (B) in plasma. The predicted concentrations of at least three-fourths of all calibration standards shall be within 15% of their individual nominal concentrations (20% for the LLQ); at least one replicate of the lowest concentration in the standard curve shall be within 20% of their nominal concentration for that level to qualify as the LLQ; and the predicted concentrations of at least three-fourths of all QC samples shall be within 15% of their individual nominal concentrations.

5.4 Pharmacokinetic Analysis

The peak plasma concentration (CMAX) and the time to reach peak concentration (TMAX) were recorded directly from experimental observations. The area under the plasma concentration-time curve from time zero to T (AUC(0–T)), where T is the time of the last measurable plasma concentration, was calculated using the trapezoidal rule (See, M. Gibaldi, et al., Pharmacokinetics, $2^{nd}$ ed., New York, N.Y., Marcel Decker, p. 445–91982). T-HALF was not determined due to the limited terminal phase sampling used in the study.

Figure 2:
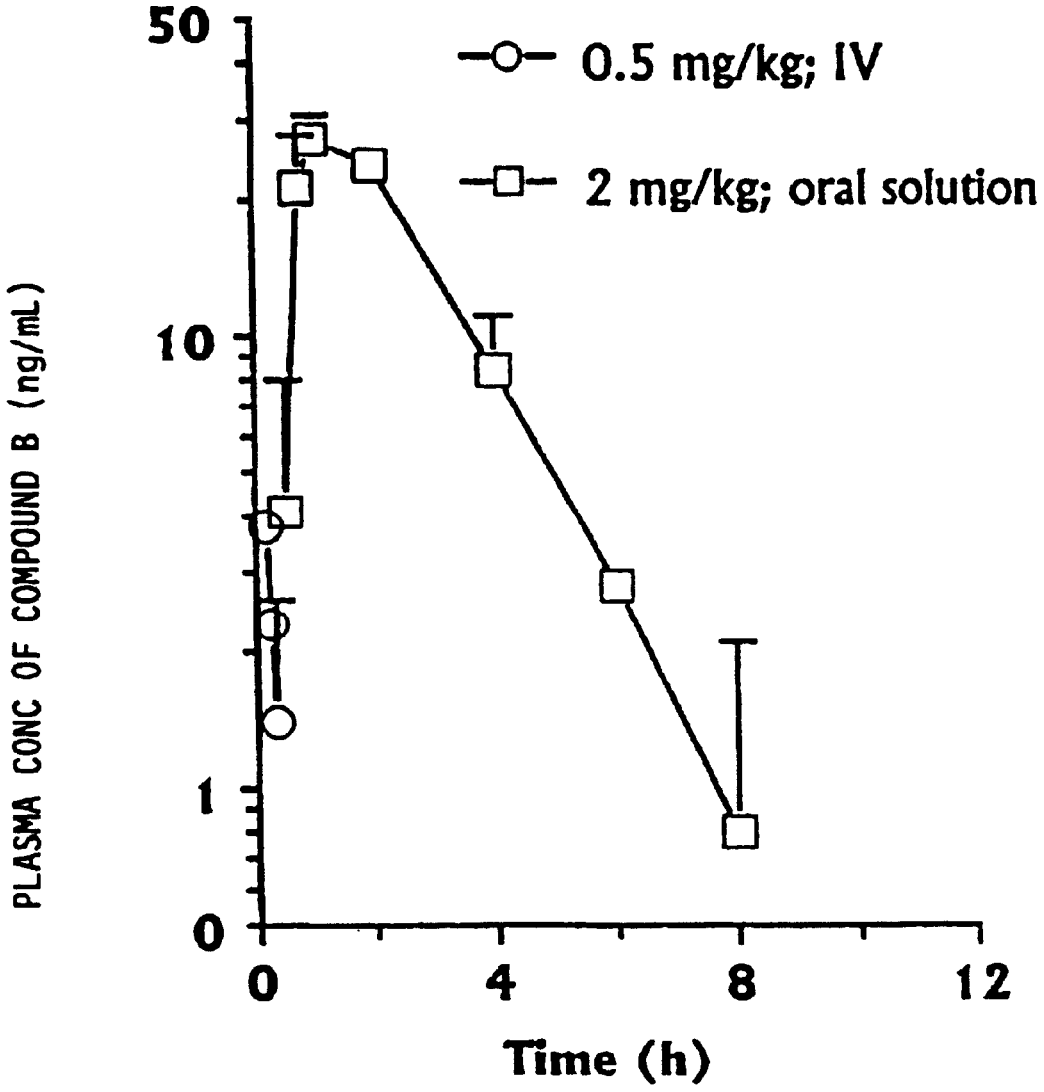
FIG. 2. Mean plasma concentration profiles for Compound (B) vs. time in dogs after IV administration at 0.5 mg/kg, -±-, and oral administration of a 2 mg/kg solution, -□-. Vertical bars represent standard deviations and are shown where larger than the symbol size.

The mean plasma concentration-time data of Compound (A) and Compound (B) are presented in Table 2. The corresponding graphical representations for Compound (A) and Compound (B) are depicted in FIGS. 1 and 2, respectively.

TABLE 2

Mean (Standard Deviation (SD)) Plasma Concentrations of Compound (A) and Compound (B) in Dogs.

| Time[a] | Mean (SD) Plasma Concentrations (mg/mL)[b] | | | |
|---|---|---|---|---|
| | Compound (A) | | Compound (B) | |
| (h) | IV[c] | Oral Solution[d] | IV[c] | Oral Solution[d] |
| Predose | 0 | 0 | 0 | 0 |
| 0.17 | 1120 (189) | —[e] | 0 | —[e] |
| 0.25 | 152 (9.9) | 251 (150) | 3.8 (0.4) | 4.1 (3.9) |

TABLE 2-continued

Mean (Standard Deviation (SD)) Plasma Concentrations of Compound (A) and Compound (B) in Dogs.

| Time[a] | Mean (SD) Plasma Concentrations (mg/mL)[b] | | | |
|---|---|---|---|---|
| | Compound (A) | | Compound (B) | |
| (h) | IV[c] | Oral Solution[d] | IV[c] | Oral Solution[d] |
| 0.33 | 73.0 (4.2) | —[e] | 2.3 (0.2) | —[e] |
| 0.5 | 38.2 (2.8) | 335 (73.8) | 1.4 (1.2) | 21.3 (6.6) |
| 0.75 | 28.6 (1.6) | 141 (75.8) | 0 | 27.2 (3.6) |
| 1 | 24.7 (3.9) | 74.1 (26.4) | 0 | 23.8 (1.7) |
| 1.5 | 20.1 (2.3) | n.s.[f] | 0 | n.s[f] |
| 2 | 17.4 (1.8) | 35.5 (7.9) | 0 | 8.4 (2.7) |
| 4 | 14.5 (1.4) | 21.8 (6.9) | 0 | 2.4 (0.3) |
| 6 | 12.6 (0.9) | 17.2 (4.7) | 0 | 0.8 (1.3) |
| 8 | 12.6 (1.7) | 17.6 (4.4) | 0 | 0 0 |
| 12 | 9.5 (1.4) | 12.8 (4.1) | 0 | 0 0 |
| 24 | 5.7 (1.3) | 7.5 (1.9) | 0 | 0 0 |

[a]Represents the nominal collection time. Minor variations from the nominal collection times were considered to have no significant impact on the overall interpretation of the results.
[b]All concentrations for the buffered oral suspension were < LLQ (2 mg/mL) and are not presented in this table. Values < LLQ were considered to be zero for mean (SD) calculations. If concentrations from all dogs at a given time was < LLQ, the mean is represented as zero.
[c]n = 3. The plasma concentration time-profile for one dog was inconsistent with the 10 min IV infusion dose since the observed TMAX was 1.0 h; this dog was omitted for calculating the mean.
[d]n = 3. One dog vomited shortly after dosing and hence was omitted for calculating the mean.
[e]Samples were not scheduled for collection.
[f]Samples were inadvertently not collected; this deviation is not considered to impact the overall conclusion from the study.

The mean pharmacokinetic parameters for Compound (A) and Compound (B) are presented in Tables 3 and 4, respectively.

TABLE 3

Mean (SD) Pharmacokinetic Parameters of Compound (A) in Dogs.

| Parameter (units) | IV[a] | Oral Solution[b] |
|---|---|---|
| CMAX (ng/mL) | 1120 (189) | 365 (40.9) |
| TMAX (h)[c] | 0.17 (0.17, 0.17) | 0.50 (0.25, 0.50) |
| AUC (0-T) (h.ng/nt)[d] | 420 (36.8) | 560 (159) |

[a]n = 3. The plasma concentration time-profile for one dog was inconsistent with the 10 min IV infusion dose since observed TMAX was 1.0 h; this dog was considered unevaluable for pharmacokinetic analyses.
[b]n = 3. One dog vomited shortly after dosing and was considered unevaluable for pharmacokinetic analyses.
[c]Median (minimum, maximum).
[d]T = 24 h.

TABLE 4

Mean (SD) Pharmacokinetic Parameters of Compound (B) in Dogs.

| Parameter (units) | IV[a] | Oral Solution[b] |
|---|---|---|
| CMAX (ng/mL) | 3.8 (0.42) | 27.2 (3.6) |
| TMAX (h)[c] | 0.17 (0.17, 0.17) | 0.75 (0.75, 0.75) |
| AUC (0-T) (h.ng/nt)[d] | 0.69 (0.15) | 45.2 (4.7) |

[a]n = 3. The Compound (A) plasma concentration time-profile for one dog was inconsistent with the 10 min IV infusion dose since observed TMAX was 1.0 h; this dog was considered unevaluable for pharmacokinetic analyses of Compound (A) and Compound (B).
[b]n = 3. One dog vomited shortly after dosing and was considered unevaluable for pharmacokinetic analyses of Compound (A) and Compound (B).
[c]Median (minimum, maximum).
[d]T = 24 h.

The plasma concentration-time profile for one dog after IV administration was inconsistent with the 10 min infusion dose since the observed TMAX was 1.0 h; this dog was not considered to be evaluable for pharmacokinetics. The mean (SD) [n=3] CMAX and AUC(0–T) values after IV administration of Compound (A) were 1120 (189) ng/mL and 420 (36.8) h.ng/nt, respectively. The AUC value obtained in this study after IV administration is reasonably comparable to the AUC values observed in a preliminary IV pharmacokinetic study (mean (SD); 483 (34) h.ng/mL) following a 0.5 mg/kg dose in dogs.

After administration of an oral buffered solution, one dog vomited shortly after dosing and hence the data from this dog were considered to be unevaluable for pharmacokinetics. The mean (SD) [n=3] CMAX, and AUC(0–T) values after administration of a buffered oral solution of Compound (A) were 365 (40.9) ng/mL and 560 (159) h.ng./mL, respectively. The mean AUC value obtained in this study after an oral solution is approximately 2-fold higher compared to the dose-normalized mean AUC value (257 h.ng/mL) obtained in a single dose oral toxicity study in dogs. Although the oral formulation for both studies was identical, the total volume of the oral solution administered in the current study was about 1.3 mL/kg while that in the toxicology study was 0.4 mL/kg. Thus the milliequivalents of buffer delivered in the current study were about 3-fold higher than those administered in the toxicology study, which may have provided better neutralization of gastric pH in the current study. Compound (A) is an acid labile drug, thus, the higher exposure after oral solution in the current study compared to the toxicology study is likely related to better protection from gastric acid degradation. For the two dogs that had pharmacokinetic parameter data after administration of both the IV and oral solution dose, the absolute oral bioavailability was 48.3% and 30.6%, respectively (means value=39.5%).

CMAX and AUC(0–T) values for Compound (B) indicates that dogs were exposed to Compound (B) after administration of the IV and oral solution dose; animals were not exposed to Compound (B) after dosing with the oral suspension. Systemic exposure to Compound (B) after oral administration was markedly higher than after IV administration.

These results show that for the two dogs that had IV and oral pharmacokinetic parameter data, the absolute oral bioavailability was 48.3% and 30.6%, respectively (mean value=39.5%).

Example 6

Liquid Oral Formulation of the Pharmaceutically acceptable acid neutralizing buffer.

Buffers were formulated having the following composition:

| Ingredient | Buffer Composition #1 Amount (g) | Buffer Composition #2 Amount (g) |
|---|---|---|
| Dibasic Sodium Phosphate Anhydrous, USP | 4.258 | 5.688 |
| Sodium Citrate Dihydrate, USP | 2.941 | 2.942 |
| Citric Acid Anhydrous, USP | 0.232 | 0.256 |
| Sucrose, NF (optional) | 15.00 | 15.00 |
| Cherry Flavor (optional) | 0.075 | 0.075 |
| Total | 22.5 | 24.0 |

The buffer is constituted with 140 mL of water to provide 150 mL of a liquid oral dosage form. The liquid oral dosage form has a pH of 7.43±0.07 (6 measurements). The average acid neutralization capacity of 5 liquid oral dosage forms was 49.7 (standard deviation 0.17, relative standard deviation 0.34%).

Example 7

Stability of a Liquid Formulation of Compound (A)

The stability of compound (A) in 80:20 propylene glycol:ethanol was evaluated by reconstituting 25 mg Compound (A) with 80:20 propylene glycol:ethanol to provide a liquid oral dosage form at concentrations of 2.5 mg/mL to 12.5 mg/mL. The resulting liquid oral dosage form was then stored up to 20 hours at ambient temperature (20° C. to 25° C.) and room light and at refrigerated temperature (2° C. to 8° C.).

No changes from initial were observed in the appearance of the liquid oral dosage form at either storage condition. An increase in total impurities/degradants and a decrease in potency were observed after storage at ambient temperature and room light for 20 hours. A slight increase in total impurities/degradants was observed after 20 hours storage at refrigerated temperature. The change in total impurities was attributed to an increase of an oxazine impurity/degradant whose structure is depicted below:

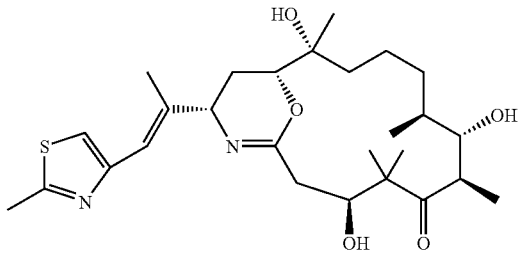

Samples were analyzed using HPLC with a 75 mm×4.6 mm i.d., 3.5 :m particle sizeWaters Symmetry Shield RP8 column and with UV detection at 240 nm. 10 :L injection volumes were used, the column was maintained at ambient temperature and the flow rate was 1 mL/min. Analysis times were 1 hour and samples were eluted using gradient elution with a mobile phase of water (0.05% acetic acid) (mobil phase A) and a mobile phase of acetonitrile (0.05% acetic acid). The elution profile is described in the table below.

| | Mobil Phase Composition | | |
|---|---|---|---|
| Time (minutes) | % A | % B | Gradient Profile |
| 0 | 90 | 10 | Isochratic |
| 3 | 90 | 10 | Isochratic |
| 43 | 40 | 60 | Linear |
| 45 | 40 | 60 | Isochratic |
| 50 | 90 | 10 | Linear |
| 60 | 90 | 10 | Isochratic |

These results demonstrate that the liquid oral dosage form, at concentrations of 2.5 mg/mL to 12.5 mg/mL, can be stored at ambient temperature for up to 6 hours and under refrigerated temperature for up to 20 hours.

Example 8

Synthesis of Compound A

[[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenylj-4-aza-17-oxabicyclo[14.1.0]heptadecane-5,9-dione.] [*1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl-4-aza-17-oxabicyclo[14.1.0]heptadecane-5,9-dione.*

Compound 1: (3S,6R,7S,8S,12R,13S,15S)-15-Azido-12,13-epoxy-4,4,6,8,12,16-hexamethyl-7-hydroxy-17-(2-methyl-4-thiazolyl)-5-oxo-16-heptadecenoic acid.

A solution of [epothione] *epothilone* B (0.35 g, 0.69 mmol) in degassed THF (4.5 mL) was treated with a catalytic amount (80 mg, 69 mmol) of tetrakis (triphenylphosphine)palladium (0) and the suspension was stirred at 25° C., under Ar for 30 min. The resulting bright yellow, homogeneous solution was treated all at once with a solution of sodium azide (54 mg, 0.83 mmol) in degassed $H_2O$ (2.2 mL). The reaction mixture was warmed to 45° C. for 1 h, diluted with $H_2O$ (5 mL) and extracted with EtOAc (4×7 mL). The organic extracts were washed with saturated aqueous NaCl (15 mL), dried [($Na_2SO4$)] $Na_2SO_4$, and concentrated in vacuo. The residue was purified by flash chromatography ([SiO2]$SiO_2$, 3.0×15 cm, 95:5.0:0.5 $CHCl_3$-MeOH-AcOH) to afford Compound 1 (0.23 g, 61%) as a colorless oil. MS ($ESI_+$): 551 $(M+H)^+$; MS(ESI−): 549 (M−H)−.

Compound 2: (3S,6R,7S,8S,12R,13S,15S)-15-Azido-12,13-epoxy-4,4,6,8,12,16-hexamethyl-7-hydroxy-17-(2-methyl-4-thiazolyl)-5-oxo-16-heptadecenoic acid.

A solution of Compound 1 (0.23 g, 0.42 mmol) in THF (4.0 mL) was treated with $H_2O$ (23 mL, 1.25 mmol) and polymer supported triphenylphosphine (Aldrich, polystyrene cross-linked with 2% DVB, 0.28 g, 0.84 mmol) at 25° C. The resulting suspension was stirred at 25° C. under Ar (32 h), filtered through a Celite pad and concentrated in vacuo. The residue was purified by flash chromatography ($SiO_2$, 1.5×10 cm, 95:5.0:0.5 to 90:10:1.0 $CHCl_3$-MeOH-AcOH gradient elution) to afford Compound 2 (96 mg, 44%) as a colorless oil. MS $(ESI^+)$: 525.2 $(M+H)^+$; MS(ESI−): 523.4 (M−H)−.

Alternatively, to a 25 mL round-bottom flask charged with Compound 1 (0.26 g, 0.47 mmol) and $PtO_2$ (0.13 g, 50 wt %) was added absolute EtOH under Ar. The resulting black mixture was stirred under one atmosphere of $H_2O$ for 10 h, after which time the system was purged with $N_2$ and an additional portion of $PtO_2$ (65 mg, 25 wt %) was added. Once again the reaction mixture was stirred under a blanket of $H_2O$ for 10 h. The system was then purged with $N_2$, and the reaction mixture was filtered through a Celite pad eluting with $CH_2Cl_2$ (3×25 mL). The solvents were removed in vacuo and the residue was purified as described above to afford Compound 2 (0.19 g, 75%).

Alternatively, a solution of Compound 1 (20 mg, 36 mmol) in THF (0.4 mL) was treated with triphenylphosphine (19 mg, 73 mmol) under Ar. The reaction mixture was warmed to 45° C., stirred for 14 h and cooled to 25° C. The resulting iminophosphorane was treated with ammonium hydroxide (28%, 0.1 mL) and once again the reaction mixture was warmed to 45° C. After 4 h, the volatiles were removed in vacuo and the residue was purified as described above to afford Compound 2 (13 mg, 70%).

Compound A: [1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenylJ-4-aza-17-oxabicyclo[14.1.0]heptadecane-5,9-dione.

A solution of Compound 2 (0.33 g, 0.63 mmol) in degassed DMF (250 mL) was treated with solid $NaHCO_3$ (0.42 g, 5.0 mmol) and [diphenylposphoryl] *diphenylphosphoryl* azide (0.54 mL, 2.5 mmol) at 0° C. under Ar. The resulting suspension was stirred at 4° C. for 24 h, diluted with phosphate buffer (250 mL, pH=7) at 0° C. and extracted with EtOAc (5×100 mL). The organic extracts were washed with 10% aqueous LiCl (2×125 mL), dried ($Na_2SO_4$) and concentrated in vacuo. The residue was first purified by flash chromatography ($SiO_2$, 2.0×10 cm, 2–5% MeOH-$CHCl_3$ gradient elution) and then repurified using a Chromatotron (2 mm $SiO_2$, GF rotor, 2–5% [MeOH-CHCls] *MeOH—$CHCl_3$* gradient elution) to afford the title compound (0.13 g, 40%) as a colorless oil: $^1$H NMR ($CDCl_3$, 400 MHz) * 6.98 (s, 1H), 6.71 (d, 1H, NH, J=8.1 Hz), 6.56 (s, 1 H), 4.69–4.62 (m, 1 H), 4.18–4.12 (m, 1 H), 4.01–3.96 (m, 1 H), 3.86 (s, 1 H), 338–3.34 (m, 1 H), 2.82 (dd, 1 H, J5.6, 6.0 Hz), 2.71 (s, 3 H), 2.58 (s, 1 H), 2.43 (dd, 1 H, J=9.0, 14.5 Hz), 3.34 (dd, 1 H, J=3.0, 14.5 Hz), 2.14 (s, 3 H), 2.05–1.92 (m, 2 H), 1.82–1.41 (a series of multiplets, 7 H), 1.35 (s, 3 H), 1.28 (s, 3 H), 1.18 (d, 3 H, J=6.8 Hz), 1.14 (s, 3 H), 1.00 (d, 3 H, J=6.8 Hz); MS ($ESI^+$): 507.2 $(M+H)^+$; MS(ESI−): 505.4 (M−H)−.

Example 9

Pharmacokinetics of Compound A Orally Administered to Cancer Patients

Patients with advanced malignancies were administered Compound A weekly as a 30-minute infusion (a course=3 intravenous weekly administrations). Patients received doses of 1, 2.5, 5, 10, 20, 25, or 30 mg/$m^2$. Starting at the 20 mg/$m^2$ dose level, a single oral dose of Compound A was given on day 6 in a vehicle of 80% propylene glycol and 20% ethanol (v/v) followed by administration of a citrate/phosphate buffer (22.5 gm) before course 1 to assess the absolute bioavailability of Compound A. The dose of oral Compound A administered on Day 6 matched the dose of IV Compound A administered on day 1. Serial plasma sampling was obtained on day 6 and day 1 of course 1 to assess pharmacokinetics by an LC/MS/MS. The LC/MS/MS assay was the same as used in Example 1.

Compound A for oral administration, 25 mg/vial, was supplied as "drug in bottle." The vehicle (buffer) for constitution of Compound A, 25 mg/vial, was a mixture of 80% propylene glycol and 20% ethanol (v/v). The propylene glycol/ethylene mixture was prepared by mixing 80 parts by volume of propylene glycol and 20 parts by volume of ethanol in a suitable container and gently swirling the container until the solution was completely mixed.

The citrate/phosphate buffer for oral administration after compound A was supplied in a separate bottle. Buffer for use with Compound A was constituted with water for injection (WFI):

Compound A was prepared for administration to patients by using a suitable syringe to slowly inject 2.5, 5, or 10 mL of the propylene glycol/ethanol mixture into the 20 cc vial containing 25 mg/vial of Compound A, to give concentrations of 10, 5, or 2.5 mg/mL, respectively, depending on the dose to be administered to the patient The syringe was removed and the vial shaken vigorously for 10 seconds. The vial was placed in a sonication bath and sonicated until the solution became clear. Vials were pooled depending on the dose.

The buffer for administration with Compound A was supplied in an 8 oz. clear glass bottle and was constituted with water for injection (WFI). The child resistant cap was removed from the bottle of buffer and about 140 mL of water for injection (WFI) were added. The bottle was shaken vigorously or sonicated with intermittent shaking until a clear solution was obtained.

Following oral administration on day 6, 7 mL blood samples was collected into Becton Dickinson Vacutainer tubes with $K_3$EDTA as anticoagulent (lavender-colored top) according to the following schedule (expressed as hours:minutes from the start of the oral administration): predose, 00:15, 00:30, 00:45, 01:00, 01:30, 02:00, 03:00, 04:00, 06:00, 08:00, 24:00, 48:00, and 72:00. Following IV administration on day 1, 7 mL blood samples were collected into Becton Dickinson Vacutainer tubes with $K_3$EDTA as anticoagulent (lavender-colored top) according to the following schedule (expressed as hours:minutes from the start of the IV infusion): predose, 00:15, 00:30 (end-of infusion), 00:45, 01:00, 01:30, 02:00, 03:00, 04:00, 06:00, 08:00, 24:00, 48:00, and 72:00.

Immediately after blood collection, the Vacutainer tubes were inverted several times to ensure mixing with the anticoagulant and then immediately placed on crushed ice. Within 30 minutes of collection, samples were centrifuged for 5 minutes at approximately 2000×g and 0 to [5 EC] *5° C.* The plasma was then transferred to separate pre-labeled screw-capped polypropylene tubes and stored at [−70 EC] *−70° C.* until bioanalysis. Plasma concentrations of Compound A were analyzed using the LC/MS/MS assay described in Example 1.

The plasma concentration versus time data were analyzed using non-compartmental methods. The pharmacokinetic parameters determined for Compound A included the maximum observed plasma concentration (Cmax), time to reach Cmax (Tmax), area under the plasma concentration time curve from time zero to the time of last sampling time T(AUC (0–T)).

A total of 18 patients have received oral Compound A as a solution on day 6 and by IV on day 1. The summary of the pharmacokinetic results from these patients is presented in Table 5.

TABLE 5

Summary of Pharmacokinetics of Patients Administered Compound (A) Orally and Intravenously

| Dose (mg/$m^2$) | 20 | | 25 | | 305 | |
|---|---|---|---|---|---|---|
| | 3 | | 11 | | 4 | |
| N | | | | | | |
| Route | IV | Oral | IV | Oral | IV | Oral |
| Formulation | IV | Solution for Oral Admin. | IV | Solution for Oral Admin. | IV | Solution for Oral Admin. |
| CMAX[a] | 251 | 142 | 447 | 180 | 711 | 274 |
| (ng/mL) | (108) | (1068) | (189) | (110) | (530) | (104) |
| TMAX[b] | 0.25 | 1.0 | 0.50 | 0.50 | 0.50 | 0.50 |

TABLE 5-continued

| | Summary of Pharmacokinetics of Patients Administered Compound (A) Orally and Intravenously | | | | | |
|---|---|---|---|---|---|---|
| Dose (mg/m$^2$) | 20 3 | | 25 11 | | 305 4 | |
| N | | | | | | |
| Route | IV | Oral | IV | Oral | IV | Oral |
| Formulation | IV | Solution for Oral Admin. | IV | Solution for Oral Admin. | IV | Solution for Oral Admin. |
| (h) | (0.25, 0.25) | (0.25, 1.50) | (0.25, 0.50) | (0.25, 3.00) | (0.25, 0.50) | (0.25, 0.75) |
| AUC(0-T)[a,c] (h. ng/mL) | 796 (589) | 404 (381) | 848 (284) | 533 (284) | 1155 (292) | 708 (291) |
| % F[a] | NA | 43.5 (16.1) | NA | 55.6 (18.4) | NA | 62.2 (25.1) |

[a]Mean (SD)
[b]Median (min, max)
[c]Represents AUC(0-T)

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of increasing the bioavailability of orally administered [epothilones] comprising orally administering to a human one or more [epothilones] *compounds* of Formula:

[

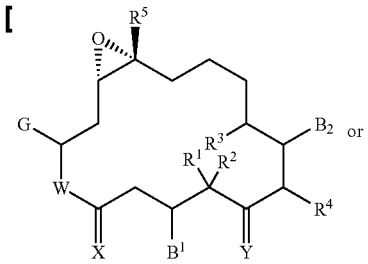

or

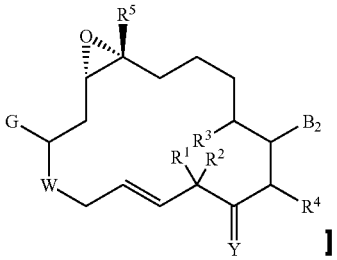

]

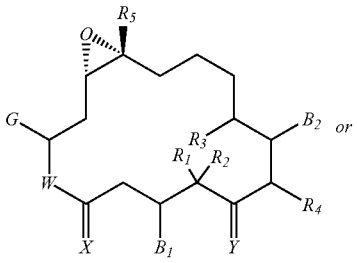

or

-continued

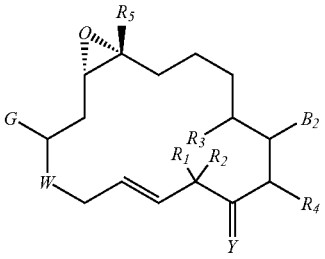

wherein:

G is [selected from the group consisting of] alkyl, substituted alkyl, aryl, substituted aryl, heterocyclo,

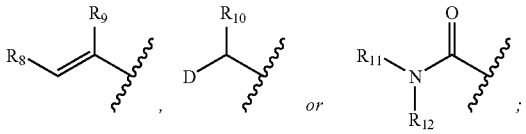

W is O or $NR^{16}$;

X is O; S; $CHR_{17}$; or H, $R_{18}$;

Y is [selected from the group consisting of] O; H, H; H, $OR_{22}$; $OR_{23}$, $OR_{23}$; $NOR_{24}$; H, [$NOR_{25}$] *$NHOR_{25}$*; H, [$HNR_{26}R_{27}$] *$NR_{26}R_{27}$*; [$NHNR_{28}R_{29}$;] H, $NHNR_{30}R_{31}$ or $CHR_{32}$, where $OR_{23}$, $OR_{23}$ can be a cyclic ketal;

$B_1$ and $B_2$ are [selected from the group consisting of] *independently* H, $OR_{33}$, $OCOR_{34}$, $OCONR_{35}R_{36}$, $NR_{37}R_{38}$, or $NR_{39}CONR_{40}R_{41}$;

D is [selected from the group consisting of] $NR_{42}R_{43}$ or heterocyclo;

$R_1$, $R_2$, $R_3$, $R_4$, and $R_5$ are [selected from] *independently* H[.] *or* lower alkyl;

$R_8$, $R_9$, $R_{10}$ and $R_{11}$ are [selected from the group consisting of] *independently* H, alkyl, substituted alkyl, aryl, substituted aryl, cycloalkyl, heterocyclo or substituted heterocyclo;

$R_{17}$, $R_{18}$, $R_{22}$, and $R_{23}$ are [selected from the group consisting of] *independently* H, alkyl, [and] *or* substituted alkyl;

$R_{24}$, $R_{25}$, $R_{26}$, [$R_{28}$,] $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{51}$, $R_{52}$, *and* $R_{53}$[, and $R_{61}$ ] are [selected from the group of] *independently* H, alkyl, substituted alkyl, aryl or substituted aryl;

$R_{12}$, $R_{16}$, $R_{27}$, [$R_{29}$,] $R_{31}$, $R_{38}$, and $R_{43}$[.] are [selected from the group consisting of] *independently* H, alkyl, substituted alkyl, substituted aryl, cycloalkyl, heterocyclo, $R_{51}C{=}O$, $R_{52}OC{=}O$, $R_{53}SO_2$, hydroxy, [and] O-alkyl or O-substituted alkyl[.]; or a pharmaceutically acceptable [salt,] solvate, clathrate, hydrate or prodrug thereof, and orally administering one or more pharmaceutically acceptable acid neutralizing buffers, *wherein the bioavailability of the compound is increased with the acid neutralizing buffer compared to that without the acid neutralizing buffer*.

2. The method of claim [1] *17*, wherein the pharmaceutically acceptable acid neutralizing buffer is administered concurrently with the [epothilone] *compound*.

3. The method of claim [1] *17*, wherein the pharmaceutically acceptable acid neutralizing buffer is administered before the [epothilone] *compound*.

4. The method of claim 3, wherein the pharmaceutically acceptable acid neutralizing buffer is administered not more than about 1 hour before the [epothilone] *compound*.

5. The method of claim [1] *17*, wherein the pharmaceutically acceptable acid neutralizing buffer is administered after the [epothilone] *compound*.

6. The method of claim 5, wherein the pharmaceutically acceptable acid neutralizing buffer is administered not more than about 1 hour after the [epothilone] *compound*.

7. The method of claim [1] *17*, wherein the pharmaceutically acceptable acid neutralizing buffer is administered before and after the [epothilone] *compound*.

8. The method of claim 7, wherein the pharmaceutically acceptable acid neutralizing buffer is administered not more than about 1 hour before and not more than about 1 hour after the [epothilone] *compound* is administered.

9. The method of claim [1] *17*, wherein the pharmaceutically acceptable acid neutralizing buffer is administered in an amount sufficient to deliver at least about 20 milliequivalents of acid neutralization capacity.

10. The method of claim [1] *17*, wherein the pharmaceutically acceptable acid neutralizing buffer is administered as an aqueous solution having a pH of between about 5 to 9.

11. The method of claim [1] *17*, wherein the pharmaceutically acceptable acid neutralizing buffer is administered as an aqueous solution comprising anhydrous dibasic sodium phosphate, sodium citrate dihydrate, and anhydrous citric acid.

12. The method of claim 11, wherein the pH of the aqueous solution is about 7.

13. The method of claim [1] *17*, wherein the bioavailability of the [one or more epothilones] *compound* or a pharmaceutically acceptable [salt,] solvate, clathrate, hydrate, or prodrug thereof is at least about 20 percent.

14. The method of claim [1] *17*, wherein the [one or more epothilones] *compound* or a pharmaceutically acceptable [salt,] solvate, clathrate, hydrate, or prodrug thereof is orally administered as a solution in propylene glycol and ethanol, wherein the [in] ratio of propylene glycol:ethanol is about 80:20.

15. The method of claim [1] *17*, wherein the [one or more epothilones] *compound* or a pharmaceutically acceptable [salt,] solvate, clathrate, hydrate, or prodrug thereof is administered in a total amount of about 0.05 to about 200 mg/kg/day.

16. The method of claim 15, wherein the [one or more epothilones of] *compound* or a pharmaceutically acceptable [salt,] solvate, clathrate, hydrate, or prodrug thereof is administered in about 2 to 4 divided doses.

17. [The method of claim 1, wherein the epothilone is [1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]heptadecane-5,9-dione.] *The method of claim 1, wherein the compound is*

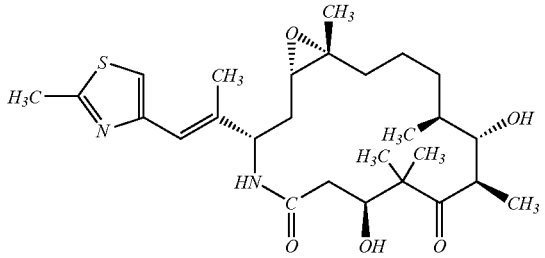

*or a pharmaceutically acceptable solvate, clathrate, hydrate, or prodrug thereof.*

18. The method of claim 1 comprising:

(a) orally administering an aqueous solution of a pharmaceutically acceptable acid neutralizing buffer comprising anhydrous dibasic sodium phosphate, sodium citrate dihydrate, and anhydrous citric acid;

(b) orally administering the one or more [epothilones] *compounds* or a pharmaceutically acceptable [salt,] solvate, clathrate, hydrate, or prodrug thereof as a solution of propylene glycol; and (c) orally administering an aqueous solution of a pharmaceutically acceptable acid neutralizing buffer comprising anhydrous dibasic sodium phosphate, sodium citrate dihydrate, and anhydrous citric acid.

19. [The method of claim 18, wherein the epothilone is [1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]heptadecane-5,9-dione.] *The method of claim 18, wherein the compound is*

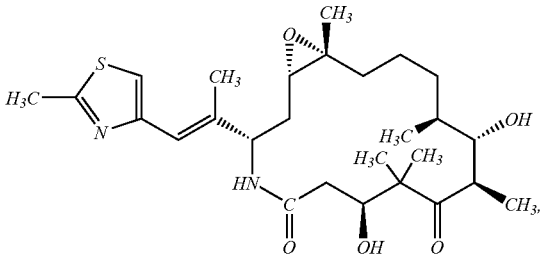

*or a pharmaceutically acceptable solvate, clathrate, hydrate, or prodrug thereof.*

20. A kit [for use in a method of increasing the bioavailability of orally administered epothilones which comprises] *comprising*:

(i) a first component comprising [one or more epothilones of Formula:

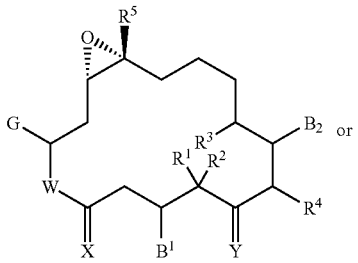

or

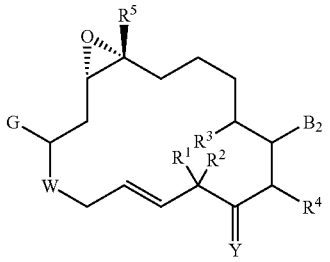

G is selected from the group consisting of alkyl, substituted alkyl, aryl, substituted aryl, heterocyclo,

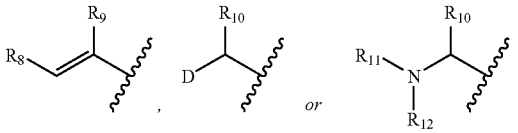

W is O or $NR^{16}$;

X is O; S; $CHR_{17}$; or H, $R_{18}$

Y is selected from the group consisting of O; H, H; H, $OR_{22}$; $OR_{23}$, $OR_{23}$; $NOR_{24}$; H, $NOR_{25}$; H, $HNR_{26}R_{27}$; $NHNR_{28}R_{29}$; H, $NHNR_{30}R_{31}$ or $CHR_{32}$, where $OR_{23}$, $OR_{23}$ can be a cyclic ketal;

$B_1$ and $B_2$ are selected from the group consisting of H, $OR_{33}$, $OCOR_{34}$, $OCONR_{35}R_{36}$, $NR_{37}R_{38}$, or $NR_{39}CONR_{40}R_{41}$ D is selected from the group consisting of $NR_{42}R_{43}$ or heterocyclo;

$R_1$, $R_2$, $R_3$, $R_4$, and $R_5$ are selected from H, lower alkyl;

$R_8$, $R_9$, $R_{10}$ and $R_{11}$ are selected from the group consisting of H, alkyl, substituted alkyl, aryl, substituted aryl, cycloalkyl, heterocyclo or substituted heterocyclo;

$R_{17}$, $R_{18}$, $R_{22}$, and $R_{23}$ are selected from the group consisting of H, alkyl, and substituted alkyl;

$R_{24}$, $R_{25}$, $R_{26}$, $R_{28}$, $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{51}$, $R_{52}$, $R_{53}$, and $R_{61}$ are selected from the group of H, alkyl, substituted alkyl, aryl or substituted aryl;

$R_{12}$, $R_{16}$, $R_{27}$, $R_{29}$, $R_{31}$, $R_{38}$, and $R_{43}$, are selected from the group consisting of H, alkyl, substituted alkyl, substituted aryl, cycloalkyl, heterocyclo, $R_{51}C{=}O$, $R_{52}OC{=}O$, $R_{53}SO_2$, hydroxy, and O-alkyl or O-substituted alkyl;] *a compound of formula*

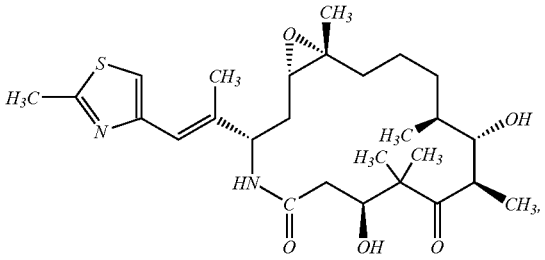

or a pharmaceutically acceptable [salt,] solvate, clathrate, hydrate, or prodrug thereof; and (ii) a second component comprising a pharmaceutically acceptable acid neutralizing buffer, wherein the first component and the second component are provided as an oral dosage form or as a pharmaceutical composition that can be reconstituted with a solvent to provide a liquid oral dosage.

21. The kit of claim 20, wherein at least one of the first component or the second component is provided as a solid oral dosage form.

22. The kit of claim 21, wherein at least one of the first component or the second component is anhydrous.

23. The kit of claim 20, wherein at least one of the first component or the second component is provided as a pharmaceutical composition that can be reconstituted with a solvent to provide a liquid oral dosage form.

24. The kit of claim 23, wherein at least one of the first component or the second component is provided as a tablet.

25. The kit of claim 23, wherein at least one of the first component or the second component is anhydrous.

26. The kit of claim 23, further comprising solvents for reconstituting the first or second components.

27. The kit of claim 26, wherein the solvent for reconstituting the first component is a mixture of propylene glycol and ethanol.

28. A pharmaceutical composition suitable for oral administration to a mammal comprising:

(i) one or more [epothilones] *compounds* of Formula:

[

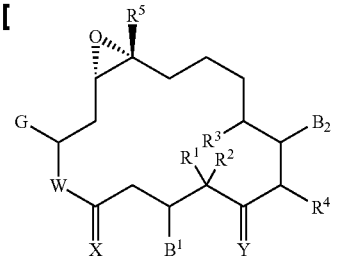

or

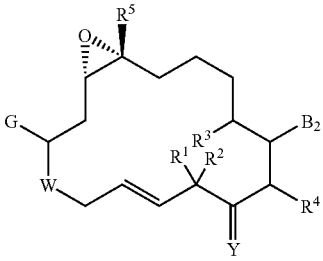

]

-continued

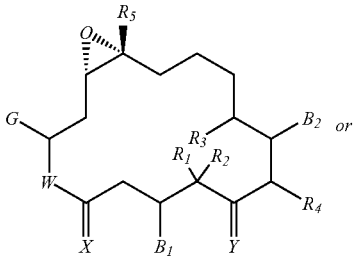

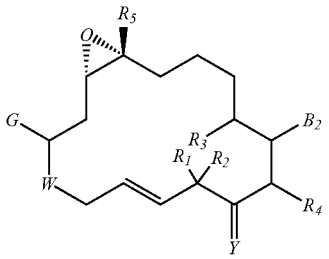

wherein:

G is [selected from the group consisting of] alkyl, substituted alkyl, aryl, substituted aryl, heterocyclo,

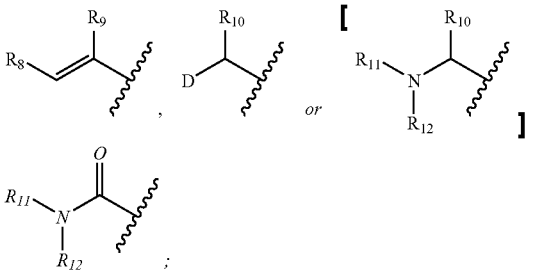

W is O or [$NR^{16}$] $NR_{16}$;

X is O; S; $CHR_{17}$; or H, $R_{18}$;

Y is [selected from the group consisting of] O; H, H; H, $OR_{22}$; $OR_{23}$, $OR_{23}$; $NOR_{24}$; H, [$NOR_{25}$] $NHOR_{25}$; H, [$HNR_{26}R_{27}$] $NR_{26}R_{27}$; [$NHNR_{28}R_{29}$;] H, $NHNR_{30}R_{31}$ or $CHR_{32}$, where $OR_{23}$, $OR_{23}$ can be a cyclic ketal;

$B_1$ and $B_2$ are [selected from the group consisting of] *independently* H, $OR_{33}$, $OCOR_{34}$, $OCONR_{35}R_{36}$, $NR_{37}R_{38}$, or $NR_{39}CONR_{40}R_{41}$ D is [selected from the group consisting of] $NR_{42}R_{43}$ or heterocyclo;

$R_1$, $R_2$, $R_3$, $R_4$, and $R_5$ are [selected from] *independently* H[,] *or* lower alkyl;

$R_8$, $R_9$, $R_{10}$ and $R_{11}$ are [selected from the group consisting of] *independently* H, alkyl, substituted alkyl, aryl, substituted aryl, cycloalkyl, heterocyclo or substituted heterocyclo;

$R_{17}$, $R_{18}$, $R_{22}$, and $R_{23}$ are [selected from the group consisting of] *independently* H, alkyl, [and] *or* substituted alkyl;

$R_{24}$, $R_{25}$, $R_{26}$, [$R_{28}$,] $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{51}$, $R_{52}$, *and* $R_{53}$[, and $R_{61}$ ] are [selected from the group of] *independently* H, alkyl, substituted alkyl, aryl or substituted aryl;

$R_{12}$, $R_{16}$, $R_{27}$, [$R_{29}$,] $R_{31}$, $R_{38}$, and $R_{43}$[,] are [selected from the group consisting of] *independently* H, alkyl, substituted alkyl, substituted aryl, cycloalkyl, heterocyclo, $R_{51}C{=}O$, $R_{52}OC{=}O$, $R_{53}SO_2$, hydroxy, [and] O-alkyl or O-substituted alkyl;

or a pharmaceutically acceptable [salt,] solvate, clathrate, hydrate, or prodrug thereof, in solid form; and (ii) a solid pharmaceutically acceptable acid neutralizing buffer in an amount sufficient to reduce decomposition of the one or more [epothilones] *compounds*, or a pharmaceutically acceptable [salt,] solvate, clathrate, hydrate, or prodrug thereof when the pharmaceutical composition is reconstituted with a solvent to provide a liquid oral dosage form.

29. The pharmaceutical composition of claim [28] *33*, wherein the pharmaceutically acceptable acid neutralizing buffer provides a liquid oral dosage form having a pH between about 5 to 9.

30. The pharmaceutical composition of claim [28] *33*, wherein the pharmaceutically acceptable acid neutralizing buffer is present in an amount sufficient to provide at least about 20 milliequivalents of acid neutralization capacity.

31. The pharmaceutical composition of claim [28] *33*, wherein the pharmaceutically acceptable acid neutralizing buffer is a dibasic phosphate-citric acid-citrate buffer.

32. The pharmaceutical composition of claim [28] *33*, wherein the [one or more epothilones] *compound* or a pharmaceutically acceptable [salt,] solvate, clathrate, hydrate, or prodrug thereof is present in an amount of between about 0.05 and 200 mg.

33. [The pharmaceutical composition of claim 28, wherein the epothilone is [1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]heptadecane-5,9-dione.] *The pharmaceutical composition of claim 28, wherein the compound is*

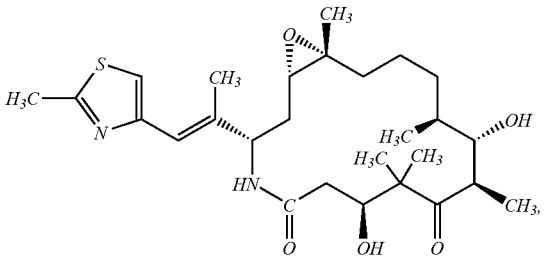

*or a pharmaceutically acceptable solvate, clathrate, hydrate, or prodrug thereof.*

34. A kit comprising the pharmaceutical composition of claim [28] *33* and a solvent for reconstituting the pharmaceutical composition to provide an oral dosage form.

35. The kit of claim 34, wherein the solvent comprises propylene glycol, ethanol, and phosphate buffer (1M, pH 8).

36. The kit of claim 35, wherein the ratio of propylene glycol:ethanol:phosphate buffer is about 58:12:30.

37. A liquid oral dosage form suitable for oral administration to a mammal comprising:

(i) one or more [epothilones] *compounds* of Formula:

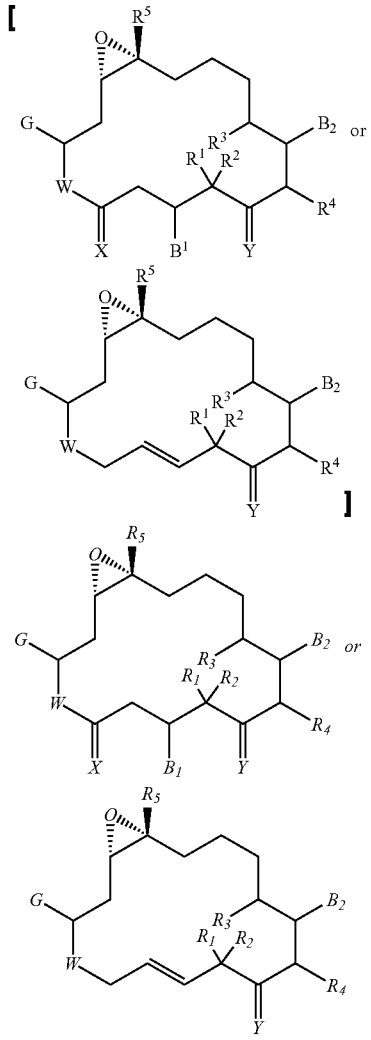

wherein:

G is [selected from the group consisting of] alkyl, substituted alkyl, aryl, substituted aryl, heterocyclo,

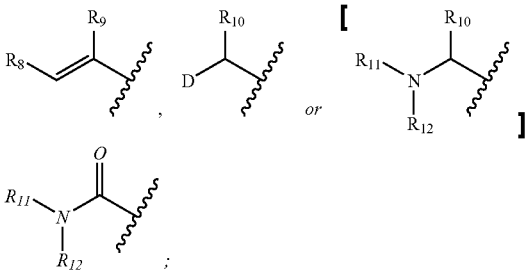

W is O or $NR^{16}$;

X is O; S; $CHR_{17}$; or H, $R_{18}$;

Y is [selected from the group consisting of] O; H, H; H, $OR_{22}$; $OR_{23}$, [$_{OR23}$] $OR_{23}$; $NOR_{24}$; H, [$NOR_{25}$] $NHOR_{25}$; H, [$HNR_{26}R_{27}$] $NR_{26}R_{27}$; [$NHNR_{28}R_{29}$;] H, $NHNR_{30}R_{31}$ or $CHR_{32}$, where $OR_{23}$, $OR_{23}$ can be a cyclic ketal;

$B_1$ and $B_2$ are [selected from the group consisting of] *independently* H, $OR_{33}$, $OCOR_{34}$, $OCONR_{35}R_{36}$, $NR_{37}R_{38}$, or $NR_{39}CONR_{40}R_{41}$ D is [selected from the group consisting of] $NR_{42}R_{43}$ or heterocyclo;

$R_1$, $R_2$, $R_3$, $R_4$, and $R_5$ are [selected from] *independently* H[,] *or* lower alkyl;

[R8, R9, R10 and R11] $R_8$, $R_9$, $R_{10}$ *and* $R_{11}$ are [selected from the group consisting of] *independently* H, alkyl, substituted alkyl, aryl, substituted aryl, cycloalkyl, heterocyclo or substituted heterocyclo;

$R_{17}$, $R_{18}$, $R_{22}$, and $R_{23}$ are [selected from the group consisting of] *independently* H, alkyl, [and] *or* substituted alkyl;

$R_{24}$, $R_{25}$, $R_{26}$, [$R_{28}$,] $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{51}$, $R_{52}$, *and* $R_{53}$[, and $R_{61}$ ] are [selected from the group of] *independently* H, alkyl, substituted alkyl, aryl or substituted aryl;

$R_{12}$, $R_{16}$, $R_{27}$, [$R_{29}$,] $R_{31}$, $R_{38}$, and $R_{43}$[,] are [selected from the group consisting of] *independently* H, alkyl, substituted alkyl, substituted aryl, cycloalkyl, heterocyclo, $R_{51}C{=}O$, $R_{52}OC{=}O$, $R_{53}SO_2$, hydroxy, [and] O-alkyl or O-substituted alkyl[,]*;* or a pharmaceutically acceptable [salt,] solvate, clathrate, hydrate, or prodrug thereof; and (ii) a pharmaceutically acceptable liquid carrier.

38. [The liquid oral dosage form of claim 37, wherein the epothilone is [1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]heptadecane-5,9-dione.] *The liquid oral dosage form of claim 37, wherein the compound is*

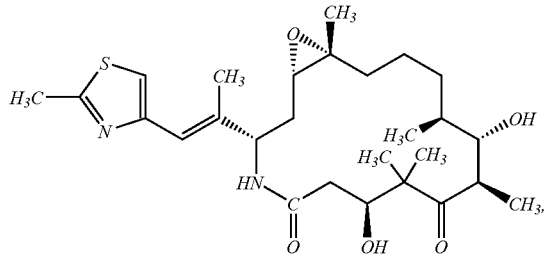

*or a pharmaceutically acceptable solvate, clathrate, hydrate, or prodrug thereof.*

39. The liquid oral dosage form of claim [37] *38*, further comprising a pharmaceutically acceptable acid neutralizing buffer in an amount sufficient to reduce decomposition of the [one or more epothilones] *compound*, or a pharmaceutically acceptable [salt,] solvate, clathrate, hydrate, or prodrug thereof compared to a pharmaceutical composition without the buffer.

40. The liquid oral dosage form of claim 39, wherein the pH of the liquid oral dosage form is between about 5 to 9.

41. The liquid oral dosage form of claim 39, wherein the buffer is present in an amount sufficient to provide at least about 20 milliequivalents of acid neutralization capacity.

42. The liquid oral dosage form of claim [37] *38*, wherein the solvent is propylene glycol, ethanol, and water buffered with a phosphate buffer at pH about 8.

43. The liquid oral dosage form of claim 42, wherein the propylene glycol, ethanol, and water buffered with a phosphate buffer are present in a ratio of about 58:12:30.

44. [The liquid oral dosage form of claim 42, wherein the epothilone is [1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]

heptadecane-5,9-dione.] *The dispersible buffered tablet of claim 48 wherein the compound is*

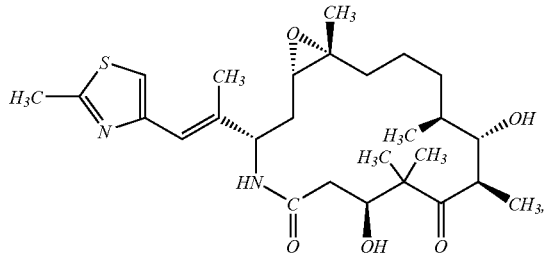

*or a pharmaceutically acceptable solvate, clathrate, hydrate, or prodrug thereof.*

45. The liquid oral dosage form of claim [37] *38*, wherein the [one or more epothilones] *compound* or a pharmaceutically acceptable [salt,] solvate, clathrate, hydrate, or prodrug thereof is present in an amount of between about 0.05 and 200 mg.

46. The liquid oral dosage form of claim 39, wherein the buffer is dibasic phosphate-citric acid-citrate buffer.

47. An article of manufacture which comprises:

(a) a sealable container suitable to carry a liquid or solid pharmaceutical;

(b) [one or more epothilones] *a compound of formula*

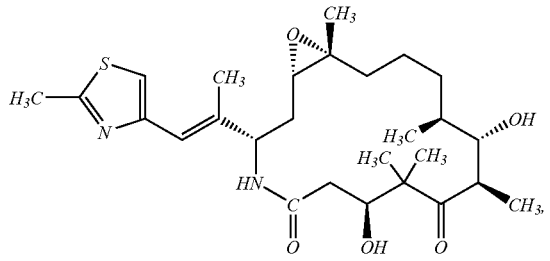

or a pharmaceutically acceptable [salt,] solvate, clathrate, hydrate or prodrug thereof; and (c) a pharmaceutically acceptable carrier suitable to deliver the [epothilone] *compound* orally.

48. A dispersible buffered tablet which comprises:

(i) one or more [epothilones] *compounds* of Formula:

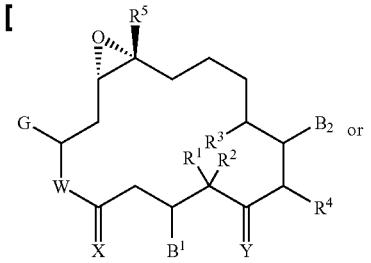

-continued

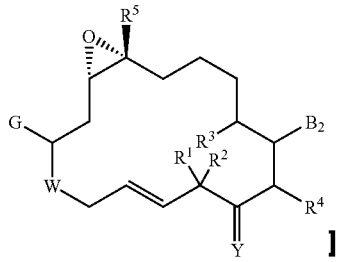

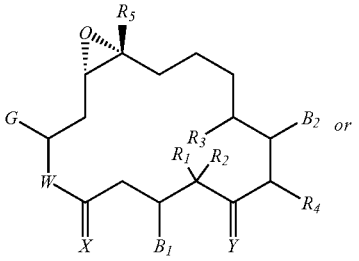

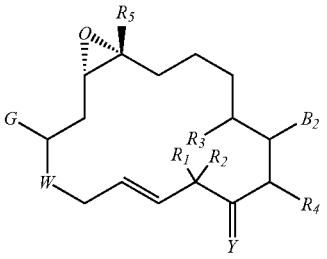

wherein:

G is [selected from the group consisting of] alkyl, substituted alkyl, aryl, substituted aryl, heterocyclo,

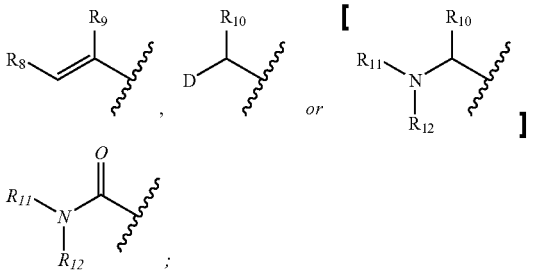

W is O or $NR^{16}$;

X is O; S; $CHR_{17}$; or H, $R_{18}$;

Y is [selected from the group consisting of] O; H, H; H, $OR_{22}$; $OR_{23}$, [$_{OR23}$] $OR_{23}$; $NOR_{24}$; H, [$NOR_{25}$] $NHOR_{25}$; H, [$HNR_{26}R_{27}$] $NR_{26}R_{27}$; [$NHNR_{28}R_{29}$;] H, $NHNR_{30}R_{31}$ or $CHR_{32}$, where $OR_{23}$, $OR_{23}$ can be a cyclic ketal;

$B_1$ and $B_2$ are [selected from the group consisting of] *independently* H, $OR_{33}$, $OCOR_{34}$, $OCONR_{35}R_{36}$, $NR_{37}R_{38}$, or $NR_{39}CONR_{40}R_{41}$ D is [selected from the group consisting of] $NR_{42}R_{43}$ or heterocyclo;

$R_1$, $R_2$, $R_3$, $R_4$, and $R_5$ are [selected from] *independently* H[,] *or* lower alkyl;

$R_8$, $R_9$, $R_{10}$ and $R_{11}$ are [selected from the group consisting of] *independently* H, alkyl, substituted alkyl, aryl, substituted aryl, cycloalkyl, heterocyclo or substituted heterocyclo;

$R_{17}$, $R_{18}$, $R_{22}$, and $R_{23}$ are [selected from the group consisting of] *independently* H, alkyl, [and] *or* substituted alkyl;

$R_{24}$, $R_{25}$, $R_{26}$, [$R_{28}$,] $R_{30}$, $R_{32}$, $R_{33}$, $R_{34}$, $R_{35}$, $R_{36}$, $R_{37}$, $R_{39}$, $R_{40}$, $R_{41}$, $R_{42}$, $R_{51}$, $R_{52}$, *and* $R_{53}$[, and $R_{61}$ ] are [selected from the group of] *independently* H, alkyl, substituted alkyl, aryl or substituted aryl;

$R_{12}$, $R_{16}$, $R_{27}$, [$R_{29}$,] $R_{31}$, $R_{38}$, and $R_{43}$[,] are [selected from the group consisting of] *independently* H, alkyl, substituted alkyl, substituted aryl, cycloalkyl, heterocyclo, [$R_{51}C{=}O$] $R_{51}C{=}O$, $R_{52}OC{=}O$, [$R_{53}SO2$] $R_{53}SO_2$, hydroxy, [and] O-alkyl or O-substituted alkyl[,]*;* or a pharmaceutically acceptable [salt,] solvate, clathrate, hydrate, or prodrug thereof; and (ii) buffer components which are suitable to neutralize gastric fluids for a time sufficient to allow said [epothilone] *compound* to be absorbed.

49. The kit of claim 20, wherein the first and second component is provided as a liquid oral dosage form.

50. The kit of claim 49, wherein the [one or more epothilones] *compound* or a pharmaceutically acceptable [salt,] solvate, clathrate, hydrate, or prodrug thereof is present in an amount of between about 0.05 and 200 mg and the pharmaceutically acceptable acid neutralizing buffer is present in an amount sufficient to provide at least about 20 milliequivalents of acid neutralization capacity.

51. The kit of claim 20, wherein the first component and the second component is provided as a pharmaceutical composition that can be reconstituted with a solvent to provide a liquid oral dosage form; the [one or more epothilones] *compound* or a pharmaceutically acceptable [salt,] solvate, clathrate, hydrate, or prodrug thereof is present as a in an amount of between about 0.05 and 200 mg; and the pharmaceutically acceptable acid neutralization buffer is present in an amount sufficient to provide at least about 20 milliequivalents of acid neutralization capacity.

52. [The kit of claim 20, wherein the epothilone is [1S-[1R*,3R*(E),7R*,10S*,11R*,16S*]]-7,11-dihydroxy 8,8, 10,12,16-pentamethyl-3-[1-methyl-2-(2-methyl-4-thiazolyl) ethenyl-17-oxa-4-azabicyclo[14.1.0]heptadecane-5,9-dione and the pharmaceutically acceptable acid neutralizing buffer comprises dibasic sodium phosphate, sodium citrate, and anhydrous citric acid.] *The kit of claim 20, wherein the pharmaceutically acceptable acid neutralizing buffer comprises dibasic sodium phosphate, sodium citrate, and anhydrous citric acid.*

*53. A method for the treatment of any one of breast cancer, lung cancer, pancreatic cancer and/or prostate cancer in a human, comprising administering to said human a therapeutically effective amount of a compound of formula*

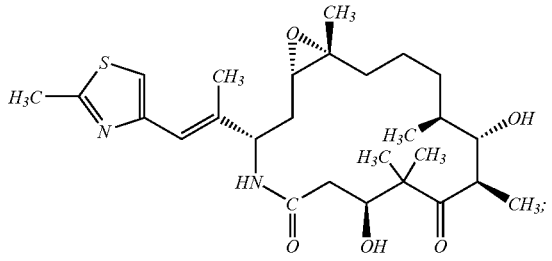

*and ketoconazole.*

*54. A method of treating any one of breast cancer, lung cancer, pancreatic cancer and/or prostate cancer in a human comprising administering to the human a therapeutically-effective combination of (1) an amount of ketoconazole and (2) an amount of a Compound (1) of formula*

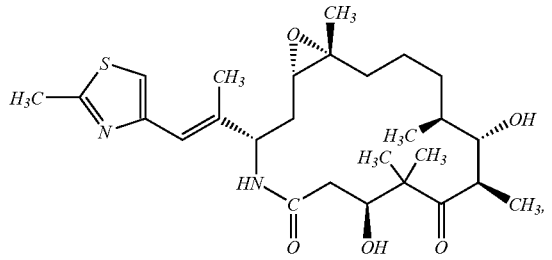

*or a pharmaceutically-acceptable solvate, clathrate, hydrate, or prodrug thereof, wherein the administration will provide an anticancer effect for a greater period of time than the effect obtainable with the amount of the Compound (1) alone.*

* * * * *